United States Patent [19]

Vu

[11] Patent Number: 6,165,999
[45] Date of Patent: Dec. 26, 2000

[54] TETRACYCLINE DERIVATIVES

[75] Inventor: Chi Bao Vu, Chestnut Hill, Mass.

[73] Assignee: Pfizer Inc, New York, N.Y.

[21] Appl. No.: 08/945,775

[22] PCT Filed: Apr. 17, 1996

[86] PCT No.: PCT/IB96/00335

§ 371 Date: Feb. 23, 1998

§ 102(e) Date: Feb. 23, 1998

[87] PCT Pub. No.: WO96/34852

PCT Pub. Date: Nov. 7, 1996

[51] Int. Cl.$^7$ ........................................ C04B 35/50
[52] U.S. Cl. ........................ 514/152; 552/203; 552/205
[58] Field of Search ................................. 552/203, 205; 514/152

*Primary Examiner*—Samuel Barts
*Attorney, Agent, or Firm*—Peter C. Richardson; Paul H. Ginsburg; Jacob M. Levine

[57] ABSTRACT

The present invention relates to novel tetracycline derivatives, to intermediates used in their preparation, to pharmaceutical compositions containing them and to their medicinal use.

19 Claims, No Drawings

TETRACYCLINE DERIVATIVES

This application is a 371 of a PCT/IB96/00335 filed Apr. 17, 1996.

BACKGROUND OF THE INVENTION

The present invention relates to novel tetracycline derivatives to intermediates used in their preparation, to pharmaceutical compositions containing them and to their medicinal use.

European Patent Publication 618,120, published Oct. 5, 1994, refers to 9-[(substituted glycyl)amido]-6-(substituted)-5-hydroxy-6-deoxytetracyclines, methods for their production and methods of using the active agents for the prevention, treatment or control of bacterial infections in warm-bloooded animals.

European Patent Publication 536,515, published Apr. 14, 1993, refers to 7-substituted-9-(substituted amino)-6-demethyl-6-deoxytetracyclines, methods for their production and methods of using the active agents for the prevention, treatment or control of bacterial infections in warm-blooded animals.

SUMMARY OF THE INVENTION

The present invention relates to compounds of the formula

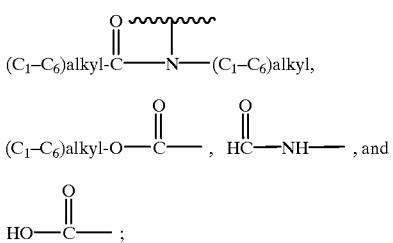

I wherein X is hydrogen;
$R^1$ is methyl;
$R^3$ is a group of the formula

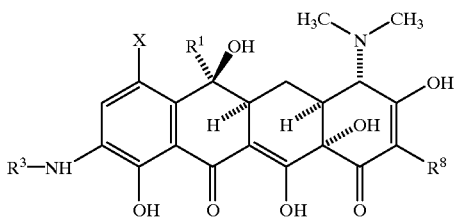

wherein n is an integar from zero to four;
$R^4$ is hydrogen or $(C_1-C_6)$alkyl;
$R^5$ is hydrogen; $(C_1-C_6)$alkyl optionally substituted with one or more substitutents, preferably one to three substituents, independently selected from methylthio, $(C_1-C_6)$alkoxy, amino, guanidino, amido, carboxamido,

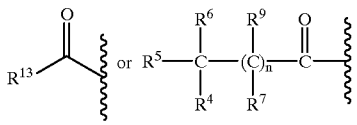

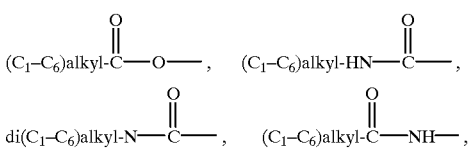

$(C_6-C_{10})$aryl—$(CH_2)_h$—, wherein h is an integer from zero to three, wherein the $(C_6-C_{10})$aryl moiety of said $(C_6-C_{10})$aryl—$(CH_2)_h$ group may optionally be substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo $(C_{1/-C6})$alkyl, amino, cyano, $(C_1-C_6)$alkylamino, di$(C_1-C_6)$alkylamino, amido, carboxamido,

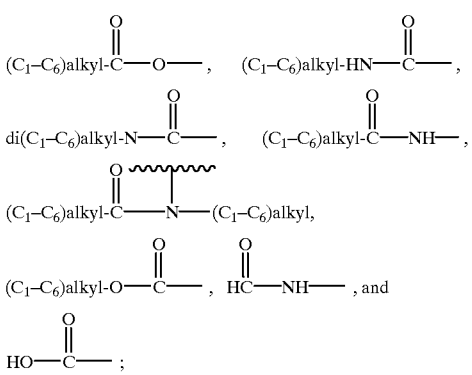

or $(C_3-C_6)$cyloalkyl—$(CH_2)_j$—, wherein j is an integer from zero to three, wherein the $(C_3-C_6)$cycloalkyl moeity of said $(C_3-C_6)$cycloalkyl—$(CH_2)_j$— group may optionally be substituted with one or more substituents, preferably one to three subsituents, independentl selected from halogen, hydroxy, $(C_1-C_6)$alkyl, $(C_1-C_6)$alkoxy, $(C_1-C_6)$alkylsulfonyl, trihalo $(C_1-C_6)$alkyl, amino, cyano, $(C_1-C_6)$alkylamino, di$(C_1-C_6)$alkylamino, amido, carboxamido,

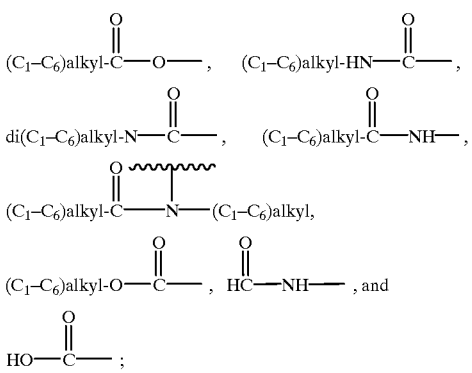

$R^6$ is halogen; amino; hydroxylamino; $(C_1-C_{12})$ alkylamino optionally substitued with one or more substituents, preferably one to three substituents, independently selected from halogen, hydroxy, $(C_1-C_6)$alkoxy, $(C_1-C_6)$alkysulfony, trihalo$(C_1-C_6)$alkyl, amino, cyano, $(C_1-C_6)$alkylamino, di$(C_1-C_6)$alkylamino, amido, carboxamido,

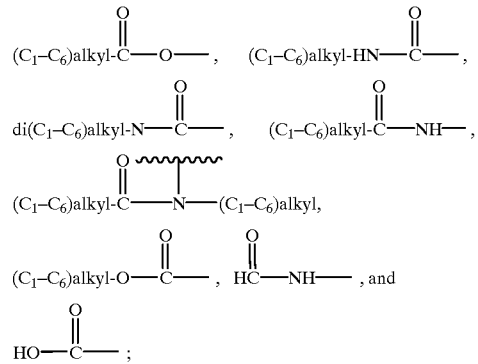

$(C_3-C_{18})$cycloaklylamino wheein the $(C_3-C_{18})$cycloalkyl moiety of said $(C_3-C_{18})$cycloalkyl amino group may optionally be substituted with one or more substituents, preferably one to three substituents, independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl,

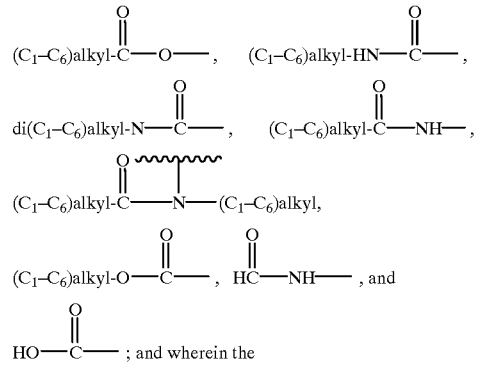

; and wherein the amino moiety of said $(C_3-C_{18})$cycloaklylamino group may optionally be substituted with $(C_1-C_6)$alkyl;

di$(C_3-C_{18})$cycloalkyl-amino optionally substituted with one or more substituents, preferably one to three substitutents, independently selected from halogen, hydroxy, $(C_1-C_6)$alkoxy, $(C_1-C_6)$alkysulfonyl, trihalo$(C_1-C_6)$alkyl, amino, cyano, $(C_1-C_6)$alkylamino, di$(C_1-C_6)$alkylamino, amido, carboxamido, $(C-C_6)$alkyl,

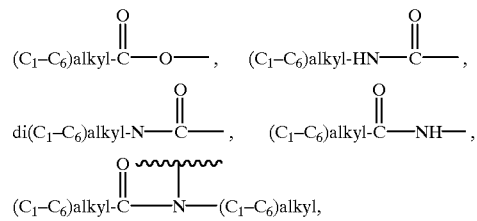

-continued

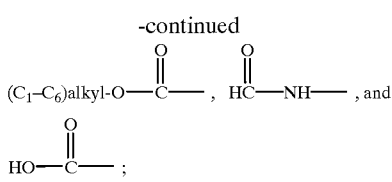

$(C_6-C_{10})$aryl—$(CH_2)_m$—amino, wherein m is an integer from zero to three, wherein the $(C_6-C_{10})$aryl moiety of said $(C_6-C_{10})$aryl—$(CH_2)_m$—amino group may optionally be substituted with one or more substituents, preferably one to three substituents, independently selected from halogen, hydroxy, $(C_1-C_6)$alkoxy, $(C_1-C_6)$alkylsulfonyl, trihalo$(C_1—C_6)$alkyl, amino, cyano, $(C_1-C_6)$alkylamino, di$(C_1-C_6)$alkylamino, amido, carboxamido, $(C_1-C_6)$alkyl,

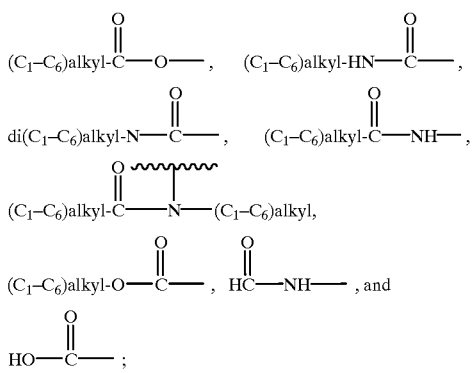

di$(C_1-C_8)$alkyl-amino optionally substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_8)$alkylamino, amido, carboxamido,

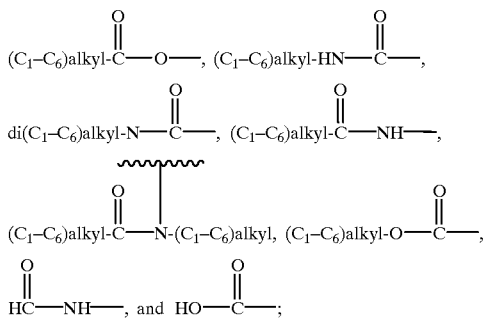

$(C_2-C_{10})$azacycloalkyl optionally substituted with one or more substituents, preferably one to three substituents, indepdently selected from halogen, hydroxy, $(C_1-C_6)$alkyl, $(C_1-C_6)$alkoxy, $(C_1-C_6)$alkysulfonyl, trihalo$(C_1-C_6)$alkyl, amino, cyano, $(C_1-C_6)$alkylamino, di$(C_1-C_6)$alkylamino, amido, carboxamido,

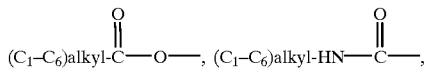

-continued

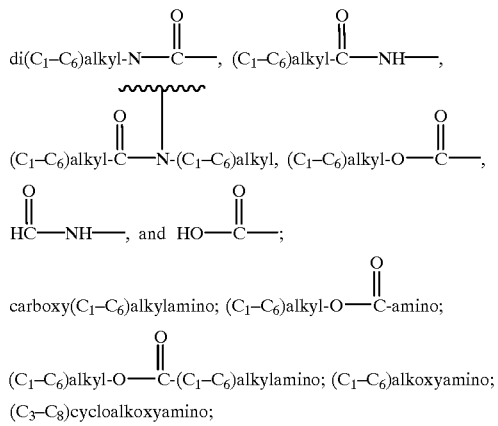

carboxy($C_1$–$C_6$)alkylamino; ($C_1$–$C_6$)alkyl-O—C(=O)—amino;

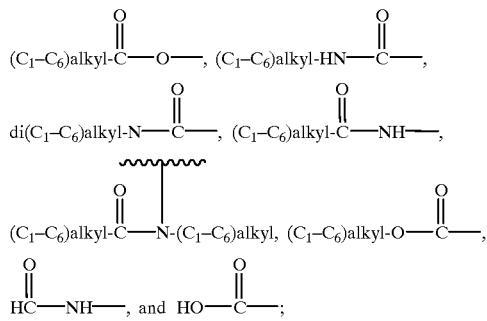

($C_6$–$C_{10}$)aryl—($CH_2$)$_t$-oxyamino, wherein t is an integer from zero to three, wherein the ($C_6$–$C_{10}$)aryl moiety of said ($C_6$–$C_{10}$)aryl—($CH_2$)$_t$-oxyamino group may optionally be substituted with one or more substituents, preferably one to three substituents, independently selected from halogen, ($C_1$–$C_6$)alkoxy, trihalo($C_1$–$C_6$) alkyl, amino, cyano, ($C_1$–$C_6$)alkylamino, hydroxy, ($C_1$–$C_6$)alkyl, ($C_1$–$C_6$)alkylsulfonyl, di($C_1$–$C_6$) alkylamino, amido, carboxamido,

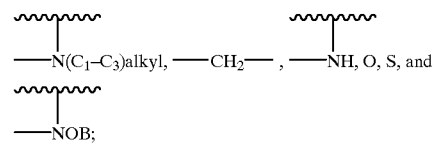

or a heterocycle—($CH_2$)$_k$—amino group, whrein k is an integer from zero to three, wherein said heterocycle is selected from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridiazinyl, 1,2,4-triazinyl, 1,2,3-triazinyl, 1,3,5-triazinyl, 1,2,5-thiadiazinyl, 1,25-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isolndolyl, indolyl, indazolyl, isoquinolyl, quinolyl, phthalazinyl, quinoxalinyl, quinazolinyl, cinnolinyl and benzoxazinyl;
wherein the heterocycle moiety of said heterocycle—($CH_2$)$_k$—group may be, where possible, substituted with from one to three substituents independently selected from ($C_1$–$C_6$)alkyl, halogen, hydroxy, cyano, ($C_1$–$C_6$)alkoxy, ($C_1$–$C_6$)alkysulfonyl, trihalo($C_1$–$C_6$) alkyl, amino, ($C_1$–$C_6$)alkylamino, di($C_1$–$C_6$) alkylamino, amido, carboxamido,

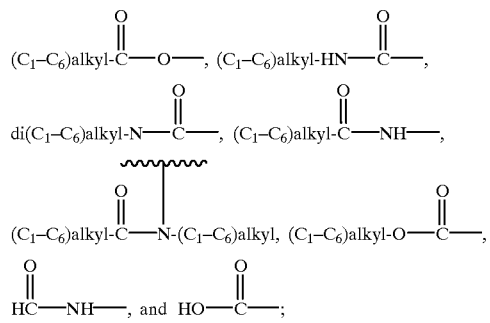

or $R^5$ and $R^6$ taken together may form a —($CH_2$)$_p$W($CH_2$)$_q$— ring wherein W is selected from

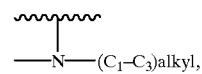

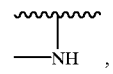

whrein B is selected from hydrogen and ($C_1$–$C_3$)alkyl, p is an integer from one to three, and q is an integer from one to three;
$R^7$ is hydrogen or ($C_1$–$C_6$)alkyl;
$R^8$ is —$CONH_2$ or —$CONHCH_2$—$NR^{11}$ $R^{12}$;
$R^9$ is hydrogen or ($C_1$–$C_6$)alkyl;
$R^{11}$ is ($C_1$–$C_6$)alkyl;
$R^{12}$ is ($C_1$–$C_6$)alkyl; or
$R^{11}$ and $R^{12}$ taken together form a —($CH_2$)$_r$—Y—($CH_2$)$_s$ ring where Y is oxygen, suflur or —NOB; wherein B is selected from hydrogen or ($C_1$–$C_3$)alkyl, r is an integer from one to three, and s is an integer from one to three;
$R^{13}$ is hydrogen, ($C_1$–$C_6$)alkoxy—($C_1$–$C_6$)alkyl, ($C_1$–$C_6$) alkyl, ($C_1$–$C_6$)alkoxy, ($C_3$–$C_6$)cycloalkyl, ($C_3$–$C_6$) cycloalkylmethyl, or ($C_6$–$C_{10}$)aryl optinally substituted with one or more substituents, preferably one to three substituents, independently selcted from fluoro, hydroxy, ($C_1$–$C_6$)alkoxy, trihalo($C_1$–$C_6$)alkyl, amino, cyano, ($C_1$–$C_6$)alkylamino, di($C_1$–$C_6$)alkylamino, amido, carboxamido,

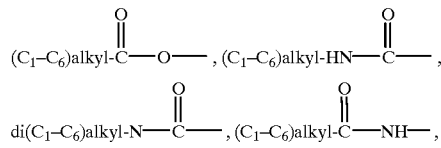

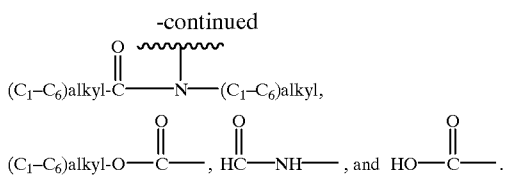

The moiety

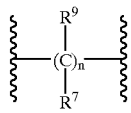

are used herein refers to a variable length carbon chain in which each carbon atom of the chain may optionally be indepenently substituted with one or both of the moieties $R^7$ and $R^9$.

The present invention also relates to the pharmaceutically acceptable acid addition salts of compounds of the formula I. The acids which are used to prepare the pharmaceutically acceptable acid adddtion salts of those compounds of formula I that are basic in nature are those which form non-toxic acid addition salts, e.g., salts containing pharmacologically acceptable anions, such as the chloride, bromide Iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [e.g., 1,1'-methylene-bis-(2-hydroxy-3-naphthoate)]salts.

The invention also relates to base additionsalts of formula I. The chemical bases that may be used as reagents to prepare pharmaceutically acceptable base salts of those compoounds of formula I that are acidic in nature are those that form non-toxic base seats with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Preferred compounds of the invention are compounds of the formula I wherein $R^8$ is —CONH$_2$.

More preferred compounds of the formula I are those wherein n is zero; $R^4$ is hydrogen; and $R^5$ is hydrogen.

Most preferred compounds of the forula I are those wherein $R^6$ is halogen, amino, hydroxylamino, $(C_1–C_{12})$ alkylamino optionally substituted with one or more substituents, preferably one to three substituents, independently selected from halogen, hydroxy, $(C_1–C_6)$alkoxy, $(C_1–C_6)$alkylsulfonyl, trihalo$(C_1–C_6)$alkyl, amino, cyano, $(C_1–C_6)$alkylamino, di$(C_1–C_6)$alkylamino, amido, carboxamido,

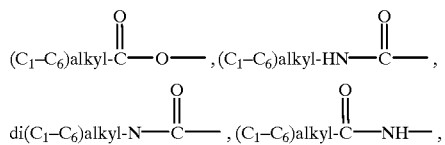

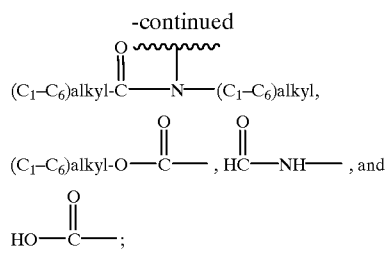

$(C_3–C_{18})$cycloalkylamino wherein the $(C_3–C_{18})$ cycloalkyl moiety of said $(C_3–C_{18})$cycloalkyl amino group may optionally be substituted with one or more substituents, preferably one to three substituents, independently selected from halogen, hydroxy, $(C_1–C_6)$ alkoxy, $(C_1–C_6)$alkylsulfonyl, trihalo$(C_1–C_6)$alkyl, amino, cyano, $(C_1–C_6)$alkylamino, di$(C_1–C_6)$ alkylamino, amido, carboxamido, $(C_1–C_6)$alkyl,

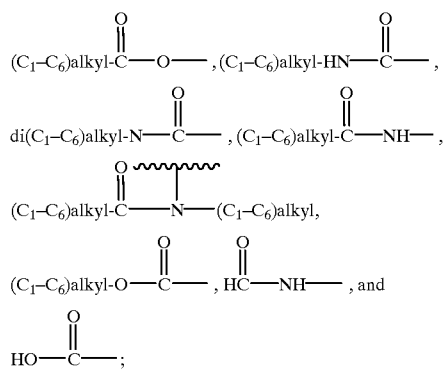

and wherein the amino moiety of said $(C_3–C_{18})$cycloalkyl amino group may optionally be substituted with $(C_1–C_6)$ alkyl;

di$(C_1–C_8)$alkyl-amino optionally substituted with one or more substituents, preferably one to three sustituents, indepedently selected from halogen, hydroxy, $(C_1–C_6)$ alkyl, $(C_1–C_6)$alkoxy, $(C_1–C_6)$alkylsulfonyl, trihalo $(C_1–C_6)$alkyl, amino, cyano, $(C_1–C_6)$alkylamino, di$(C_1 1\,C_6)$alkylamino, amido, carboxamido,

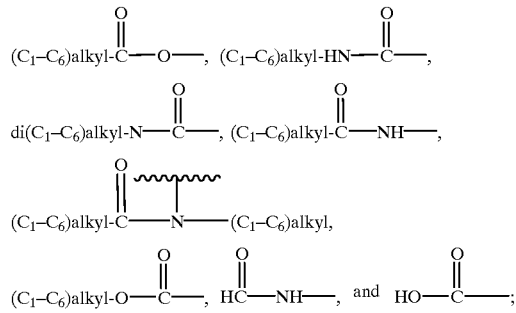

$(C_2–C_{10})$azacycloalkyl optionally substituted with one or more substituents, preferably one to three substituents, independently selected from halogen, hydroxy, $(C_1–C_6)$alkyl, $(C_1–C_6)$alkoxy, $(C_1–C_6)$alkylsulfonyl, trihalo$(C_1–C_6)$alkyl, amino, cyano, $(C_1–C_6)$ alkylamino, di$(C_1–C_6)$alkylamino, amido, carboxamido,

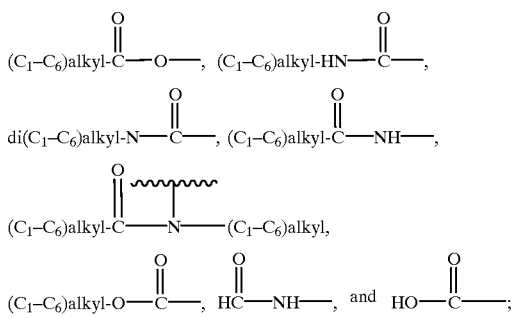

or $R^5$ and $R^6$ taken together may for a $—(CH_2)_pW(CH_2)_q—$ ring wherein W is selected from

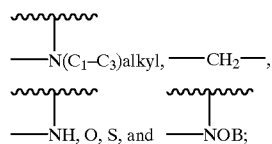

whrein B is selected from hydrogen and $(C_1–C_3)$alkyl, p is an integer from one to three, and q is an integer from one to three.

The followng compounds of formula I are particularly preferred:

9-[(N,N-dimethylaminoacetyl)amino]tetracycline;
9-[(tert-butylaminoacetyl)amino]tetracycline;
9-[(N-methyl-N'-tert-butylaminoacetyl)amino]tetracycline;
9-[(diisopropylaminoacetyl)amino]tetracycline;
9-[(pyrrolidinoacetyl)amino]tetracycline;
9-[(cycloheptylaminoacetyl)amino]tetracycline; and
9-[(tert-amylaminoacetyl)amino]tetracycline.

Other compounds of the invention include:
9-[(n-butylaminoacetyl)amino]tetracycline;
9-[(isopropylaminoacetyl)amino]tetracycline;
9-[(n-pentylaminoacetyl)amino)amino]tetracycline;
9-[(piperidinoacetyl)amino]tetracycline;
9-[(azetidinoacetyl)amino]tetracycline;
9-[(n-hexlaminoacetyl)amino]tetracycline;
9-[(cyclohexylaminoacetyl)amino]tetracycline;
9-[(N-methyl-n-butylaminoacetyl)amino]tetracycline;
9-[(3-ethoxypropylaminoacetyl)amino]tetracycline;
9-[(3-dimethylaminopropylaminoacetyl)amino]tetracycline; 9-[(diethylaminoacety)amino]tetracycline;
9-[(cyclopentylaminoacetyl)amino]tetracycline;
9-[(hexylaminoacetyl)amino]tetracycline;
9-[(1-methylapiperazineacetyl)amino]tetracycline;
9-[(cyclobutlaminoacetyl)amino]tetracycline;
9-[(homopiperidinoacetyl)amino]tetracycline;
9-[(methylcyclopropylaminoacetyl)amino]tetracycline;
9-[(ethylaminoacetyl)amino]tetracycline;
9-[(3-methoxypropylaminoacetyl)amino]tetracycline;
9-[(methylaminoacetyl)amino]tetracycline;
9-[(isoamylaminoacetyl)amino]tetracycline;
9-[(N-ethylisopropylaminoacetyl)amino]tetracycline;
9-[(benzylaminoacetyl)amino]tetracycline;
9-[(diisobutylaminoacetyl)amino]tetracycline;
9-[(N-methylcyclohexcylaminoacetyl)amino]tetracycline;
9-[(N-methylisopropylaminoacetyl)amino]tetracycline;
9-[(cyclooctylaminoacetyl)amino]tetracycline;
9-[(cyclopropylaminoacetyl)amino]tetracycline;
9-[(isobutylaminoacetyl)amino]tetracycline;
9-[(para-trifluormethylbenzylaminoacetyl)amino]tetracycline;
9-[(N-methylethylaminoacetyl)amino]tetracycline;
9-[(N-methylproplaminoacetyl)amino]tetracycline;
9-[N-ethylbutylaminoacetyl)amino]tetracycline;
9-[N-ethylcyclohexylaminoacetyl)amino]tetracycline;
9[(glycylacetyl)amino]tetracycline;
9-[(L-alanylacetyl)amino]tetracycline;
9-[(L-valylacetyl)amino]tetracycline;
9-[(L-phenylalanylacetyl)amino]tetracycline;
9-[(L-glutamylacetyl)amino]tetracycline;
9-[(D-alanylacetyl)amino]tetracycline;
9-[(D-valylacetyl)amino]tetracycline;
9-[(D-phenylalanylacetyl)amino]tetracycline;
9-[(D-glutamylacetyl)amino]tetracycline;
9-(L-alanylamino)tetracycline;
9-(L-valylamino)tetracycline;
9-(L-phenylalanylamino)tetracycline;
9-(L-glutamylamino)tetracycline;
9-(D-alanylamino)tetracycline;
9-(D-valylamino)tetracycline;
9-(D-phenylalanylamino)tetracycline; and
9-(D-glutamylamino)tetracycline.

The present invention also relates to compounds of the formula

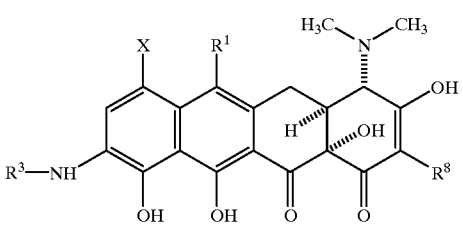

II wherein X is hydrogen or chlorine, $R^1$ is hydrogen or methyl, and $R^3, R^4, R^5, R^6, R^7, R^8, R^9, R^{11}, R^{12}$ and $R^{13}$ are as defined above for formula I. These compounds are useful as antibiotics.

The present invention also relates to the pharmaceutically acceptable acid addition salts of compounds of the formula II. The acids which are used to prepare the pharmaceutically acceptable acid addition salts to those compunds of formula II that are basic in nature are those which form non-toxic acid addition salts, e.g., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzensulfonate, p-toluenesulfonate and pamoate [e.g., 1,1'-methylene-bis-(2-hydroxy-3-naphthoate)]salts.

The invention also relates to base addition salts of formula II. The chemical bases that may be used as reagents to prepare pharmaceutically acceptable base salts of those compounds of formula I that are acidic in nature are those that form non-toxic base salts with such compounds. Such non-toxic base salts include, but are not limited to, those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(magiumine), and the lower alkanolammonium and other base salts of pharmaceutically acceptable organic amines.

Preferred compounds of formula II are those wherein $R^8$ is —$CONH_2$.

More preferred coompounds of the formula II are those wherein n is zero; $R^4$ is hydrogen; and $R^5$ is hydrogen.

Most preferred compounds of the formula II are werhein $R^6$ is halogen, amino, hydroxylamino, $(C_1-C_{12})$ alkylamino optionally substituted with one or more substituents, preferably one to three substituents, independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido,

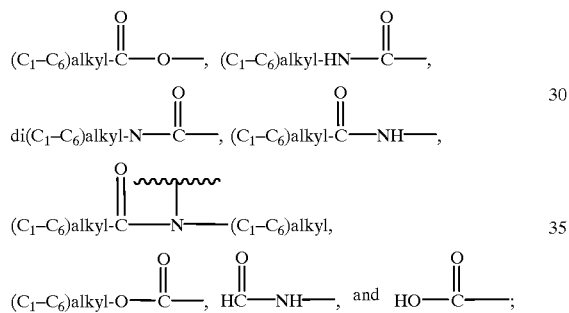

$Z(C_3-C_{18})$cycloalkylamino wherein the $(C_3-C_{18})$ cycloalkyl moiety of said $(C_3-C_{18})$cycloalkyl amino group may optionally be substituted with one or more substituents, preferably one to three subsituents, independently selected from halogen, hydroxy, $(C_1-C_6)$ alkoxy, $(C_1-C_6)$alkylsulfonyl, trihalo$(C_1 C_6)$alkyl, amino, cyano, $(C_1-C_6)$alkylamino, di$(C_1-C_6)$ alkylamino, amido, carboxamido, $(C_1-C_6)$alkyl,

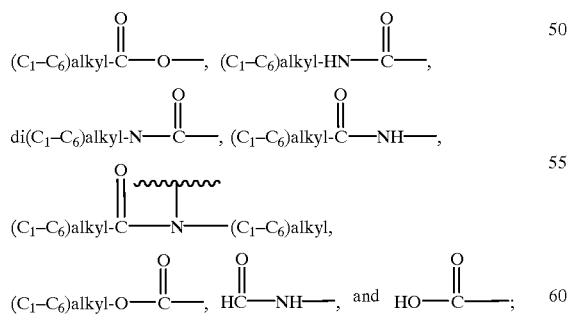

and wehrein the amino moiety of said $(C_3-C_{18})$cycloalkyl amino group may optionally be substituted with $(C_1-C_6)$ alkyl;

di$(C_1-C_8)$alkyl-amino optionally substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1 1 C_6)$ alkylamino, di$(C_1-C_6)$alkylamino, amido, carboxamido,

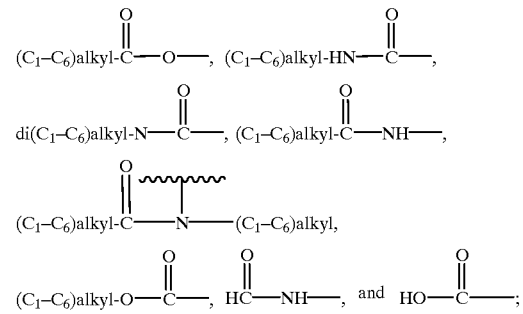

$(C_1-C_{10})$azacycloalkyl optionally substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$ alkylamino, di$(C_1-C_6)$alkylamino, amido, carboxamido,

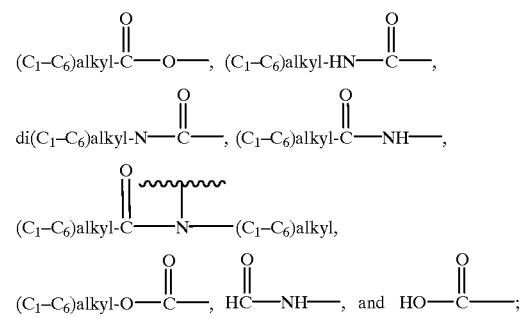

or $R^5$ and $R^6$ taken together may form a —$(CH_2)_p W(CH_2)_q$— ring wherein W is selected from

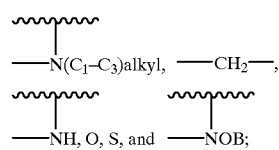

—NH, O, S, and —NOB;

wherein B is selected from hydrogen and $(C_1-C_3)$alkyl, p is an integer from one to three, and q is an integer from one to three.

The following compounds of formula II are particularly preferred:
  9-[(N,N-dimethylaminoacetyl)amino] anhydrotetracycline;
  9-[(tert-butylaminoacetyl)amino]anhydrotetracycline;
  9-[(N-methyl-N'-tert-butylaminoacetyl)amino] anhydrotetracycline;
  9-[(diisopropylaminoacetyl)amino]anhydrotetracycline;
  9-[(pyrrolidinoacetyl)amino]anhydrotetracycline;
  9-[(cycloheptylaminoacetyl)amino]anhydrotetracycline; and
  9-[(tert-amylaminoacetyl)amino]anhydrotetracycline.

Other compounds of formula II of the invention include:
9-[(bromoacetyl)amino]anhydrotetracycline;
9-[(chloroacetyl)amino]anhydrotetracycline;
9-[(N,N-dimethylaminoacetyl)amino]-7-chloro-6-demethylanhydrotetracycline;
9-[(tert-butylaminoacetyl)amino]-7-chloro-6-demethylanhydrotetracycline;
9-[(N-methyl-N'-tert-butylaminoacetyl)amino]-7-chloro-6-demethylanhydrotetracycline;
9-[(diisopropylaminoacetyl)amino]-7-chloro-6-demethylanhydrotetracycline;
9-[(pyrrolidinoacetyl)amino]-7-chloro-6-demethylanhydrotetracycline;
9-[(cycloheptylaminoacetyl)amino]-7-chloro-6-demethylanhydrotetracycline;
9-[(tert-amlaminoacetyl)amino]-7-chloro-6-demethylanhydrotetracycline;
9-[(N,N-dimethylaminoacetyl)amino]-6-demethylanhydrotetracycline;
9-[(tert-butylaminoacetyl)amino]-6-demethylanhydrotetracycline;
9-[(N-methyl-N'-tert-butylaminoacetyl)amino]-6-demethylanhydrotetracycline;
9-[(diisopropylaminoacetyl)amino]-6-demethylanhydrotetracycline;
9-[(pyrrolidinoacetyl)amino]-6-demethylanhydrotetracycline;
9-[(cycloheptylaminoacetyl)amino]-6-demethylanhydrotetracycline; and
9-[(tert-amylaminoacetyl)amino]-6-demethylanhydrotetracycline.
9-[(n-butylaminoacetyl)amino]anhydrotetracycline;
9-[(isopropylaminoacetyl)amino]anhydrotetacycline;
9-[(n-pentylaminoacetyl)amino)amino]anhydrotetracycline;
9-[(piperidinoacetyl)amino]anhydrotetracycline;
9-[(azetidinoacetyl)amino]anhydrotetracycline;
9-[(n-hexlaminoacetyl)amino]anhydrotetracycline;
9-[(cyclohexylaminoacetyl)amino]anhydrotetracycline;
9-[(N-methyl-n-butylaminoacetyl)amino]anhydrotetracycline;
9-[(3-ethoxypropylaminoacetyl)amino]anhydrotetracycline;
9-[(3-deimethylaminopropylaminoacetyl)amino]anhydrotetracycline;
9-[(diethylaminoacety)amino]anhydrotetracycline;
9-[(cyclopentylaminoacetyl)amino]anhydrotetracycline;
9-[(hexylaminoacetyl)amino]anhydrotetracycline;
9-[(1-methylpiperazineacetyl)amino]anhydrotetracycline;
9-[(cyclobutylaminoacetyl)amino]anhydrotetracycline;
9-[(homopiperidinoacetyl)amino]anhydrotetracycline;
9-[(methylcyclopropylaminoacetyl)amino]anhydrotetracycline;
9-[(ethylaminoacetyl)amino]anhydrotetracycline;
9-[(3-methoxypropylaminoacetyl)amino]anhydrotetracycline;
9-[(methylaminoacetyl)amino]anhydrotetracycline;
9-[(isoamylaminoacetyl)amino]anhydrotetracycline;
9-[(N-ethylisopropylaminoacetyl)amino]anhydrotetracycline;
9-[(benzylaminoacetyl)amino]anhydrotetracycline;
9-[(diisobutylaminoacetyl)amino]anhydrotetracycline;
9-[(N-methylcyclohexcylaminoacetyl)amino]anhydrotetracycline;
9-[(N-methylisopropylaminoacetyl)amino]anhydrotetracycline;
9-[(cyclooctylaminoacetyl)amino]anhydrotetracycline;
9-[(cyclopropylaminoacetyl)amino]anhydrotetracycline;
9-[(isobutylaminoacetyl)amino]anhydrotetracycline;
9-[(para-trifluoromethylbenzylaminoacetyl)amino]anhydrotetracycline;
9-[(N-methylethylaminoacetyl)amino]anhydrotetracycline;
9-[(N-methylpropylaminoacetyl)amino]anhydrotetracycline;
9-[(N-ethylbutylaminoacetyl)amino]anhydrotetracycline;
9-[(N-ethylcyclohexylaminoacetyl)amino]anhydrotetracycline;
9-[(N,N-dimethylaminoacetyl)amino]-7-chloro-6-demethylanhydrotetracycline;
9-[(t-butylaminoacetyl)amino]-7-chloro-6-demethylanhydrotetracycline;
9-[(n-butylaminoacetyl)amino]-7-chloro-6-demethylanhydrotetracycline;
9-[(isopropylaminoacetyl)amino]-7-chloro-6-demethylanhydrotetracycline;
9-[(n-pentylaminoacetyl)amino)amino]-7-chloro-6-demethylanhydrotetracycline;
9-[(piperidinoacetyl)amino]-7-chloro-6-demethylanhydrotetracycline;
9-[(azetidinoacetyl)amino]-7-chloro-6-demethylanhydrotetracycline;
9-[(n-hexlaminoacetyl)amino]-7-chloro-6-demethylanhydrotetracycline;
9-[(pyrrolidinoacetyl)amino]-7-chloro-6-demethylanhydrotetracycline;
9-[(cyclohexylaminoacetyl)amino]-7-chloro-6-demethylanhydrotetracycline;
9-[(cycloaheptylaminoacetyl)amino]-7-chloro-6-demethylanhydrotetracycline;
9-[(N-methyl-n-butylaminoacetyl)amino]-7-chloro-6-demethylanhydrotetracycline;
9-[(N-methyl-t-butylaminoacetyl)amino]-7-chloro-6-demethylanhydrotetracycline;
9-[(3-ethoxypropylaminoacetyl)amino]-7-chloro-6-demethylanhydrotetracycline;
9-[(tert-amylaminoacetyl)amino]-7-chloro-6-demethylanhydrotetracycline;
9-[(3-dimethylaminopropylaminoacetyl)amino]-7-chloro-6-demethylanhydrotetracycline;
9-[(diethylaminoacety)amino]-7-chloro-6-demethylanhydrotetracycline;
9-[(cyclopentylaminoacetyl)amino]-7-chloro-6-demethylanhydrotetracycline;
9-[(hexylaminoacetyl)amino]-7-chloro-6-demethylanhydrotetracycline;
9-[(1-methylpiperazineacetyl)amino]-7-chloro-6-demethylanhydrotetracycline;
9-[(cyclobutylaminoacetyl)amino]-7-chloro-6-demethylanhydrotetracycline;
9-[(homopiperidinoacetyl)amino]-7-chloro-6-demethylanhydrotetracycline;

9-[(methylcyclopropylaminoacetyl)amino]-7-chloro-6-demethylanhydrotetracycline;
9-[(ethylaminoacetyl)amino]-7-chloro-6-demethylanhydrotetracycline;
9-[(3-methoxypropylaminoacetyl)amino]-7-chloro-6-demethylanhydrotetracycline;
9-[(methylaminoacetyl)amino]-7-chloro-6-demethylanhydrotetracycline;
9-[(isoamylaminoacetyl)amino]-7-chloro-6-demethylanhydrotetracycline;
9-[(N-ethylisopropylaminoacetyl)amino]-7-chloro-6-demethylanhydrotetracycline;
9-[(benzylaminoacetyl)amino]-7-chloro-6-dememthylanhydrotetracycline;
9-[(diisopropylaminoacetyl)amino]-7-chloro-6-demethylanhydrotetracycline;
9-[(diisobutylaminoacetyl)amino]-7-chloro-6-demethylanhydrotetracycline;
9-[(N-methylcyclohexcylaminoacetyl)amino]-7-chloro-6-demethylanhydrotetracycline;
9-[(N-methylisopropylaminoacetyl)amino]-7-chloro-6-demethylanhydrotetracycline;
9-[(cyclooctylaminoacetyl)amino]-7-chloro-6-demethylanhydrotetracycline;
9-[(cyclopropylaminoacetyl)amino]-7-chloro-6-demethylanhydrotetracycline;
9-[(isobutylaminoacetyl)amino]-7-chloro-6-demethylanhydrotetracycline;
9-[(para-trifluoromethylbenzylaminoacetyl)amino]-7-chloro-6-demethylanhydrotetracycline;
9-[(N-methylethylaminoacetyl)amino]-7-chloro-6-demethylanhydrotetracycline;
9-[(N-methylpropylaminoacetyl)amino]-7-chloro-6-demethylanhydrotetracycline;
9-[(N-ethylbutylaminoacetyl)amino]-7-chloro-6-demethylanhydrotetracycline;
9-[(N-ethylcyclohexylaminoacetyl)amino]-7-chloro-6-demethylanhydrotetracycline;
9-[(N,N-dimethylaminoacetyl)amino]-6-demethylanhydrotetracycline;
9-[(t-butylaminoacetyl)amino]-6-demethylanhydrotetracycline;
9-[(n-butylaminoacetyl)amino]-6-demethylanhydrotetracycline;
9-[(isopropylaminoacetyl)amino]-6-demethylanhydrotetracycline;
9-[(n-pentylaminoacetyl)amino)amino]-6-demethylanhydrotetracycline;
9-[(piperidinoacetyl)amino]-6-demethylanhydrotetracycline;
9-[(azetidinoacetyl)amino]-6-demethylanhydrotetracycline;
9-[(n-hexylaminoacetyl)amino]-6-demethylanhydrotetracycline;
9-[(pyrrolidinoacetyl)amino]-6-demethylanhydrotetracycline;
9-[(cyclohexylaminoacetyl)amino]-6-demethylanhydrotetracycline;
9-[(cycloheptylaminoacetyl)amino]-6-demethylanhydrotetracycline;
9-[(N-methyl-n-butylaminoacetyl)amino]-6-demethylanhydrotetracycline;
9-[(N-emthyl-t-butylaminoacetyl)amino]-6-demethylanhydrotetracycline;
9-[(3-ethoxypropylaminoacetyl)amino]-6-demethylanhydrotetracycline;
9-[(tert-amylaminoacetyl)amino]-6-demethylanhydrotetracycline;
9-[(3-dimethylaminopropylaminoacetyl)amino]-6-demethylanhydrotetracycline;
9-[(diethylaminoacety)amino]-6-demethylanhydrotetracycline;
9-[(cyclopentylaminoacetyl)amino]-6-demethylanhydrotetracycline;
9-[(hexylaminoacetyl)amino]-6-demethylanhydrotetracycline;
9-[(1-methylpiperazineacetyl)amino]-6-demethylanhydrotetracycline;
9-[(cyclobutylaminoacetyl)amino]-6-demethylanhydrotetracycline;
9-[(homopiperidinoacetyl)amino]-6-demethylanhydrotracycline;
9-[(methylcyclopropylaminoacetyl)amino]-6-demethylanhydrotetracycline;
9-[(ethylaminoacetyl)amino]-6-demethylanhydrotetracycline;
9-[(3-methyoxyproplaminoacetyl)amino]-6-demethylanhydrotetracycline;
9-[(methylaminoacetyl)amino]-6-demethylanhydrotetracycline;
9-[(isoamylaminoacetyl)amino]-6-demethylanhydrotetracycline;
9-[(N-ethylisopropylaminoacetyl)amino]-6-demethylanhydrotetracycline;
9-[(benzylaminoacetyl)amino]-6-demethylanhydrotetracycline;
9-[(diisopropylaminoacetyl)amino]-6-demethylanhydrotetracycline;
9-[(diisobutylaminoacetyl)amino]-6-demethylanhydrotetracycline;
9-[(N-methylcyclohexcylaminoacetyl)amino]-6-demethylanhydrotetracycline;
9-[(N-methylisopropylaminoacetyl)amino]-6-demethylanhydrotetracycline;
9-[(cyclooctylaminoacetyl)amino]-6-demethylanhydrotetracycline;
9-[(cyclopropylaminoacetyl)amino]-6-demethylanhydrotetracycline;
9-[(isobutylaminoacetyl)amino]-6-demethylanhydrotetracycline;
9-[(para-trifluoromethylbenzylaminoacetyl)amino]-6-demethylanhydrotetracycline;
9-[(N-methylethylaminoacetyl)amino]-6-demethylanhydrotetracycline;
9-[(N-methylpropylaminoacetyl)amino]-6-demethylanhydrotetracycline;
9-[(N-ethylbutylaminoacetyl)amino]-6-demethylanhydrotetracycline;
9-[(N-ethylcyclohexylaminoacetyl)amino]-6-demethylanhydrotetracycline;
9-[(glycylacetyl)amino]anhydrotetracycline;
9-[(L-alanylacetyl)amino]anhydrotetracycline;
9-[(L-valylacetyl)amino]anhydrotetracycline;
9-[(L-phenylalanylacetyl)amino]anhydrotetracycline;
9-[(L-glutamylacetyl)amino]anhydrotetracycline;
9-[(D-alanylacetyl)amino]anhydrotetracycline;
9-[(D-valylacetyl)amino]anhydrotetracycline;

9-[(D-phenylalanylacetyl)amino]anhydrotetracycline;
9-[(D-glutamylacetyl)amino]anhydrotetracycline;
9-(L-alanylamino)anhydrotetracycline;
9-(L-valylamino)anhydrotetracycline;
9-(L-phenylalnylamino)anhydrotetracycline;
9-(L-glutamylamino)anhydrotetracycline;
9-(D-alanylamino)anhydrotetracycline;
9-(D-valylamino)anhydrotetracycline;
9-(D-phenylalnylamino)anhydrotetracycline;
9-(D-glutamylamino)anhydrotetracycline;
9-[(glycylacetyl)amino]-7-chloro-6-demethylanhydrotetracycline;
9-[(L-alanylacetyl)amino]-7-chloro-6-demethylanhydrotetracycline;
9-[(L-valylacetyl)amino]-7-chloro-6-demethylanhydrotetracycline;
9-[(L-phenylalanylacetyl)amino]-7-chloro-6-demethylanhydrotetracycline;
9-[(L-glutamylacetyl)amino]-7-chloro-6-demethylanhydrotetracycline;
9-[(D-alanylacetyl)amino]-7-chloro-6-demethylanhydrotetracycline;
9-[(D-valylacetyl)amino]-7-chloro-6-demethylanhydrotetracycline;
9-[(D-phenylalanylacetyl)amino]-7-chloro-6-demethylanhydrotetracycline;
9-[(D-glutamylacetyl)amino]-7-chloro-6-demethylanhydrotetracycline;
9-(L-alanylamino)-7-chloro-6-demethylanhydrotetracycline;
9-(L-valylamino)-7-chloro-6-demethylanhydrotetracycline;
9-(L-phenylalnylamino)-7-chloro-6-demethylanhydrotetracycline;
9-(L-glutamylamino)-7-chloro-6-demethylanhydrotetracycline;
9-(D-alanylamino)-7-chloro-6-demethylanhydrotetracycline;
9-(D-valylamino)-7-chloro-6-demethylanhydrotetracycline;
9-(D-phenylalnylamino)-7-chloro-6-demethylanhydrotetracycline;
9-(D-glutamylamino)-7-chloro-6-demethylanhydrotetracycline;
9-[(glycylacetyl)amino]-6-demethylanhydrotetracycline;
9-[(L-alanylacetyl)amino]-6-demethylanhydrotetracycline;
9-[(L-valylacetyl)amino]-6-demethylanhydrotetracycline;
9-[(L-phenylalanylacetyl)amino]-6-demethylanhydrotetracycline;
9-[(L-glutamylacetyl)amino]-6-demethylanhydrotetracycline;
9-[(D-alanylacetyl)amino]-6-demethylanhydrotetracycline;
9-[(D-valylacetyl)amino]-6-demethylanhydrotetracycline;
9-[(D-phenylalanylacetyl)amino]-6-demethylanhydrotetracycline;
9-[(D-glutamylacetyl)amino]-6-demethylanhydrotetracycline;
9-(L-alanylamino)-6-demethylanhydrotetracycline;
9-(L-valylamino)-6-demethylanhydrotetracycline;
9-(L-phenylalnylamino)-6-demethylanhydrotetracycline;
9-(L-glutamylamino)-6-demethylanhydrotetracycline;
9-(D-alanylamino)-6-demethylanhydrotetracycline;
9-(D-valylamino)-6-demethylanhydrotetracycline;
9-(D-phenylalnylamino)-6-demethylanhydrotetracycline; and
9-(D-glutamylamino)-6-demethylanhydrotetracycline;

The present invention also relates to useful intermediates of the formula

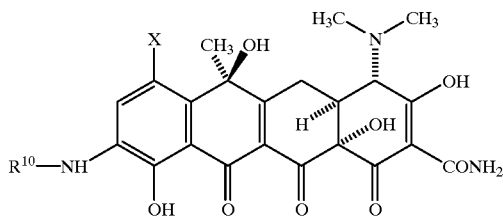

wherein $R^{10}$ is a group of the formula

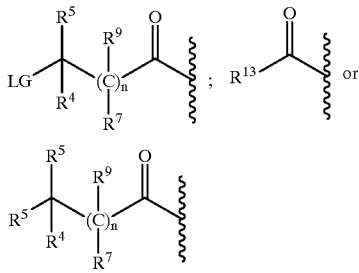

LG is chloro, bromo, iodo, —OSO$_2$Ph, —OSO$_2$PhCH$_3$, —OSO$_2$CH$_3$, or —OSO$_2$CH$_3$;

and wherein X, n, $R^4$, $R^5$, $R^6$, $R^7$, $R^9$, $R^{11}$, $R^{12}$ and $R^{13}$ are as defined above for formula I.

Preferred compounds of the formula III are those wherein X is hydrogen and $R^8$ is —CONH$_2$.

More preferred compounds of the formula III are those wherein n is zero; $R^4$ is hydrogen; and $R^5$ is hydrogen.

Most preferred compounds of the formula III are those wherein $R^6$ is halogen, amino, hydroxylamino, (C$_1$–C$_{12}$) alkylamino optionally substituted with one or more substituents, preferably one to three substituents, independently selected from halogen, hydroxy, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido,

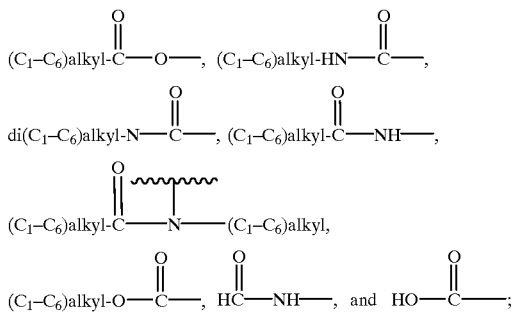

(C$_3$–C$_{18}$)cycloalkylamino wherein the (C$_3$–C$_{18}$) cycloalkyl moiety of said (C$_3$–C$_{18}$)cycloalkyl amino group may optionally be substituted with one or more substituents, preferably one to three substituents, independently selected from halogen, hydroxy, (C$_1$–C$_6$)alkoxy, (C$_1$–C$_6$) alkylsulfonyl, trihalo(C$_1$–C$_6$)alkyl, amino, cyano, (C$_1$–C$_6$) alkylamino, di(C$_1$–C$_6$)alkylamino, amido, carboxamido, (C$_1$–C$_6$)alkyl,

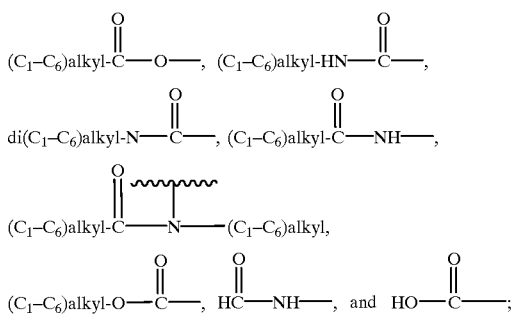

amino moiety of said $(C_3-C_{18})$cycloalkyl amino group may optionally be substituted with $(C_1-C_6)$alkyl;

di$(C_1-C_8)$alkyl-amino optionally substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo$(C_1-C_8)$alkyl, amino, cyano, $(C_1-C_6)$alkylamino, di$(C_1-C_6)$alkylamino, amido, carboxamido,

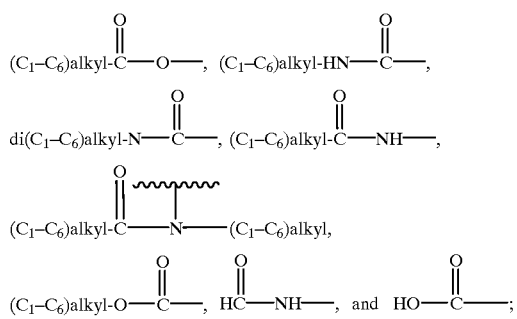

$(C_2-C_{10})$azacycloalkyl optionally substituted with one or more substituents, preferably one to three substituents, independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido,

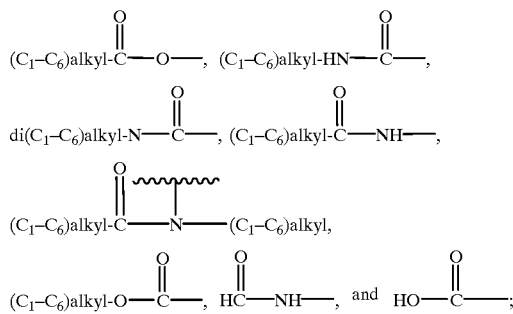

or $R^5$ and $R^6$ taken together may form a $-(CH_2)_pW(CH_2)_q-$ ring wherein W is selected from

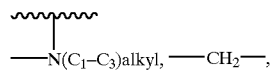

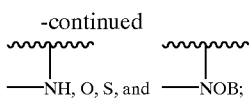

wherein B is selected from hydrogen and $(C_1-C_3)$alkyl, p is an integer from one to three, and q is an integer from one to three.

The present invention also relates to a method for the prevention, treatment or control of bacterial infections in warm-blooded animals which comprises administering to said animal a pharmacologically effective amount of a compound of formula I, as defined above.

The present invention also relates to a pharmaceutical composition for the prevention, treatment or control of bacterial infections in warm-blooded animals which comprises a pharmacologically effective amount of a compound of formula I, as defined above, in association with a pharmaceutically acceptable carrier.

The present invention also relates to a method for the prevention, treatment or control of bacterial infections in warm-blooded animals which comprises administering to said animal a pharmacologically effective amount of a compound of formula II, as defined above.

The present invention also relates to a pharmaceutical composition for the prevention, treatment or control of bacterial infections in warm-blooded animals which comprises a pharmacologically effective amount of a compound of formula II, as defined above, in association with a pharmaceutically acceptable carrier.

The present invention also relates to a method for treating or preventing osteoarthritis in mammals which comprises administering to said mammal a pharmacologically effective amount of a compound of formula I, as described above.

The present invention also relates to a pharmaceutical compositions for treating or preventing osteoarthritis in mammals which comprises a pharmacologically effective amount of a compound of formula I, as defined above, in association with a pharmaceutically acceptable carrier.

$(C_1-C_6)$Alkyl, when used herein, refers to straight or branched alkyl groups such as methyl, ethyl, n-propyl, 1-methylethyl, n-butyl, 1-methyl-propyl, 2-methylpropyl or 1,1-dimethylethyl.

$(C_3-C_6)$Cycloalkyl, when used herein, refers to saturated carbocyclic groups such as cyclopropyl, cyclobutyl, cyclopentyl or cyclohexyl.

Di$(C_1-C_6)$alkyl-amino, when used herein, refers to straight or branched alkyl amino groups such as ethyl(1-methylethyl)amino, diisopropyl amino, and methyl propyl amino.

$(C_6-C_{10})$Aryl, when used herein, refers to such groups as phenyl, naphthyl or β-naphthyl.

$(C_7-C_9)$Aryl—$(CH_2)_n$—, when used herein, refers to such groups as benzyl, 1-phenylethyl, 2-phenylethyl or phenylpropyl.

$(C_2-C_8)$Azacycloalkyl, when used herein, refers to saturated nitrogen containing carbocycles such as pyrrolidine, piperidine, azetidine, homopiperidine, heptamethyleneimine, piperazine, and N-methylpiperazine.

$(C_1-C_6)$alkylamino, refers to straight or branched alkyl groups which terminate in an amino group. Included in this group are such groups as aminomethyl, aminoethyl, aminopropyl or aminobutyl.

Carboxy-$(C_1-C_6)$alkylamino, refers to amino acids in which the point of attachment is the amine moiety and the acid can be separated from the amine by a variable length alkyl chain. Included in this group are such groups as aminoacetic acid, aminobutyric acid, aminopropionic acid, β-amino propionic acid, or β-amino butyric acid.

Hydroxy($C_1$–$C_6$)alkyl, when used herein, refers to such groups as hydroxymethyl, hydroxyethyl, hydroxy-1-methylethyl or hydroxypropyl.

($C_1$–$C_6$)Alkoxyamino, when used herein, refers to such groups as methoxyamino, ethoxyamino, n-propoxyamino, 1-methylethoxyamino, n-butoxyamino, 2-methylpropoxyamino, and 1,1-dimethylethoxyamino.

($C_3$–$C_8$)Cyclaoalkoxy, when used herein, refers to saturated carbocyclic groups covalently bonded to an oxygen heteroatom. The oxygen heteroatom forms the point of attachment. Included in this group are such groups as cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2,2,1]hept-2-yloxy, and bicylo[2.2.2]oct-2-yloxy and the diastereomers and enantiomers of said ($C_3$–$C_8$)cycloalkoxy group.

($C_3$–$C_{18}$)Cycloalkylamino, when used herein, refers to saturated carbocyclic groups covalently bonded to a nitrogen heteroatom. The nitrogen heteroatom forms the point of attachment. Included in this group are such groups as cyclopropylamino, cyclobutylamino, cyclohexylamino, cyclodecylamino, adamantylamino, bicyclobutylamino, bicyclodecylamino, and bicyclootadecylamino.

Heterocycle—$(CH_2)_k$—, when used herein, refers to various heterocycles which are linked to the parent nucleus via an alkyl chain. One of ordinary skill in the art will understand that the phrase "wherein the heterocycle moiety of said heterocycle—$(CH_2)_k$— group may be, where possible, substituted with from one to three substituents" refers to the condition that any one of the substituents may form a covalent bond with each nitrogen or sulfur heteroatom or a carbon atom when that heteroatom or carbon atom possesses less than the maximum number of bonds possible. One of ordinary skill in the art will also understand that the heterocycle moiety may be connected to the alkyl chain via one of the ring heteroatoms or carbon atoms.

($C_6$–$C_{10}$)Aryl—$(CH_2)_r$-oxyamino, when used herein, refers to such groups as phenoxyamino, naphthyloxyamino or β-naphthyloxy amino.

The group

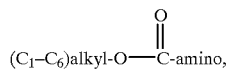

when used herein, refers to such groups as methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino.

Halogen, when used herein, refers to fluorine, chlorine, bromine or iodine.

The term "warm-blooded animals" when used herein refers to such animals as mammals, fish and birds. "Tetracycline sensitive microorganisms" when used herein refers to those microorganisms that are still susceptible to known tetracycline compounds such as oxytetracycline, chlorotetracycline, tetracycline, 7-chloro-6-demethyltetracycline, 6-demethyltetracycline, doxycycline, methacycline, and minocycline.

"Tetrayclline resistant microorganisms" when used herein refers to those microorganisms that are no longer susceptible to most of the known tetracycline compounds listed above. Two major mechanisms of bacterial resistance to these tetracyclines are: a) energy-dependent efflux of the antibiotic mediated by proteins located in the cytoplasmic membrane which prevents intracellular accumulation of tetracyclines (S. B. Levy, et al., *Antimicrob. Agents Chemotherapy* 33, 1373–1374 (1989); and b) ribosomal protection mediated by a cytoplasmic protein which interacts with the ribosome such that tetracycline no longer binds or inhibits protein synthesis (A. A. Salyers, B. S. Speers and N. B. Shoemaker, *Mol. Microbiol,* 4:151–156, 1990). The efflux mechanism of resistance is encoded by resistance determinants designated tetA-tetL. They are common in many Gram-negative bacteria (resistance genese Class A–E), such as Enterobacteriaceae, Pseudomonas, Haemophilus and Aeromonas, and in Gram-positive bacteria (resistance genes Class K and L), such as Staphylococcus, Bacillus and Streptococcus. The ribosomal protection mechanism of resistance is encoded by resistance determinants designated TetM, N and O, and is common in Staphylococcus, Streptococcus, Camptylobacter, Gardnerella, Haemophilus and Mycoplasma (A. A. Salyers, B. S. Speers and N. B. Shoemaker, *Mol. Microbiol,* 4:151–156 1990).

A particularly useful tetracycline compound is 7-(dimethylamino)-6-demethyl-6-deoxytetracycline, known as minocycline (se U.S. Pat. Nos. 3,148,212, RE 26,253 and 3,226,436). However, strains harboring the TetB (efflux in gram-negative bacteria) mechanism, but not tetK (efflux in Staphylococcus) are resistant to minocycline. Also, strains carrying tetM (ribosomal protection) are resistance to minocycline. The compounds of the present invention demonstrate significant in vitro and in vivo activity in tetracycline and minocycline susceptible strains and some tetracycline and minocycline resistant strains, that is, those harboring the tetM (ribosomal protection) resistance determinants.

DETAILED DESCRIPTION OF THE INVENTION

In the reaction Schemes and description which follow h, j, k, m, n, p, q, r, s, X, $R^1$, $R^3$, $R^4$, $R^5$, $R^6$, $R^7$, $R^8$, $R^9$, $R^{10}$, $R^{11}$, $R^{12}$, and $R^{13}$ as well as structural formulae I, II and III are as defined above.

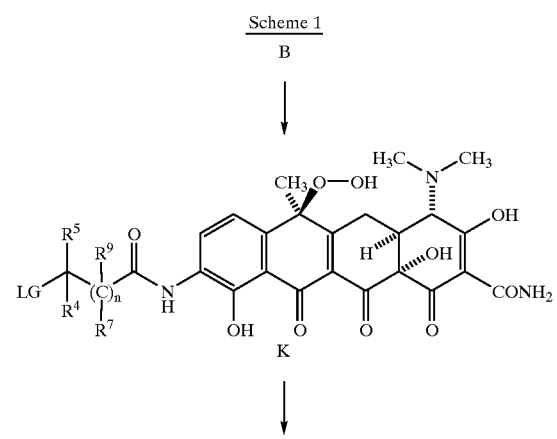

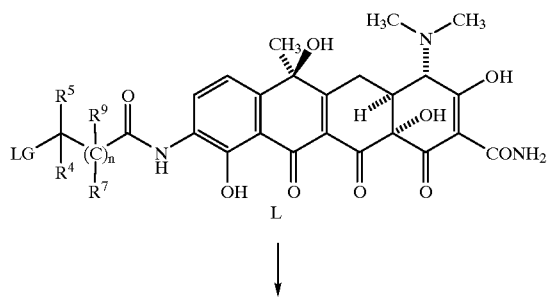
L
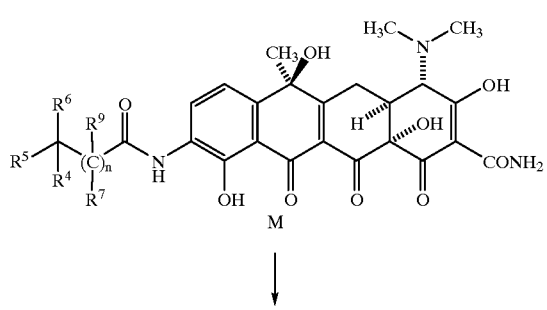
M
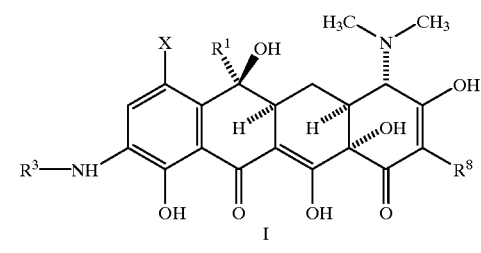
I
Scheme 2
A
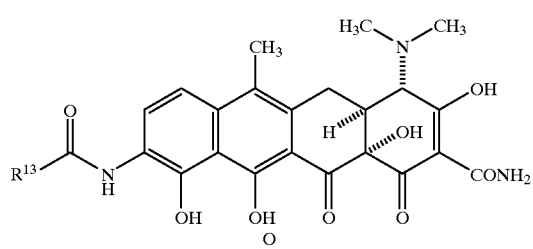
O
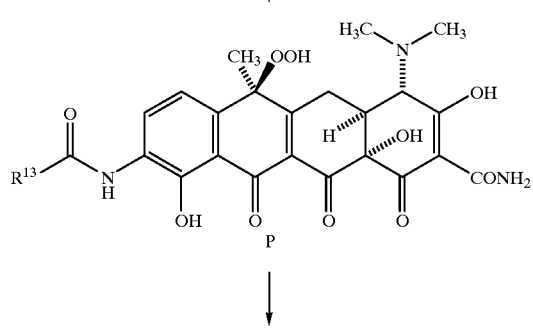
P
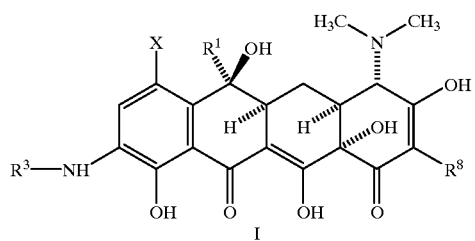
I
Scheme 3
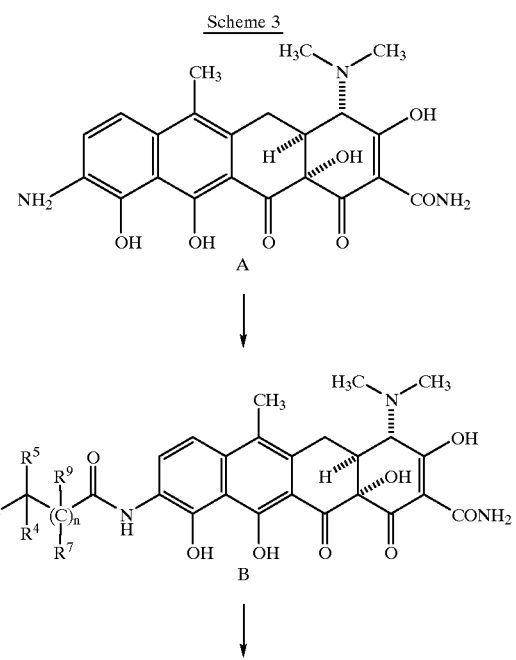
A
B
II
Scheme 4
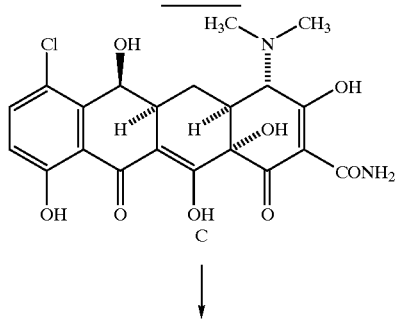
C

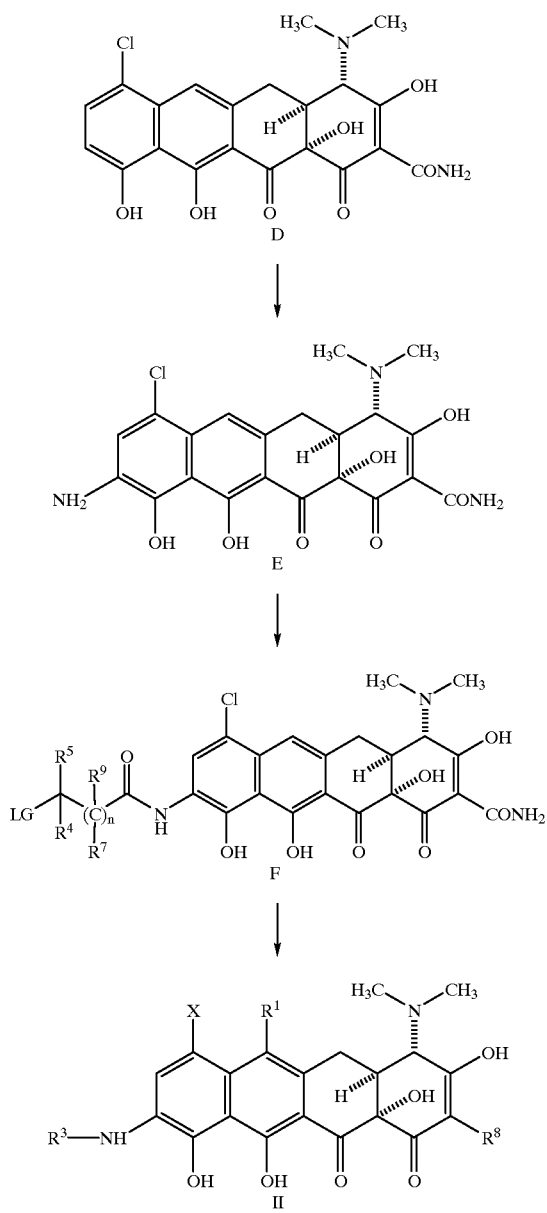

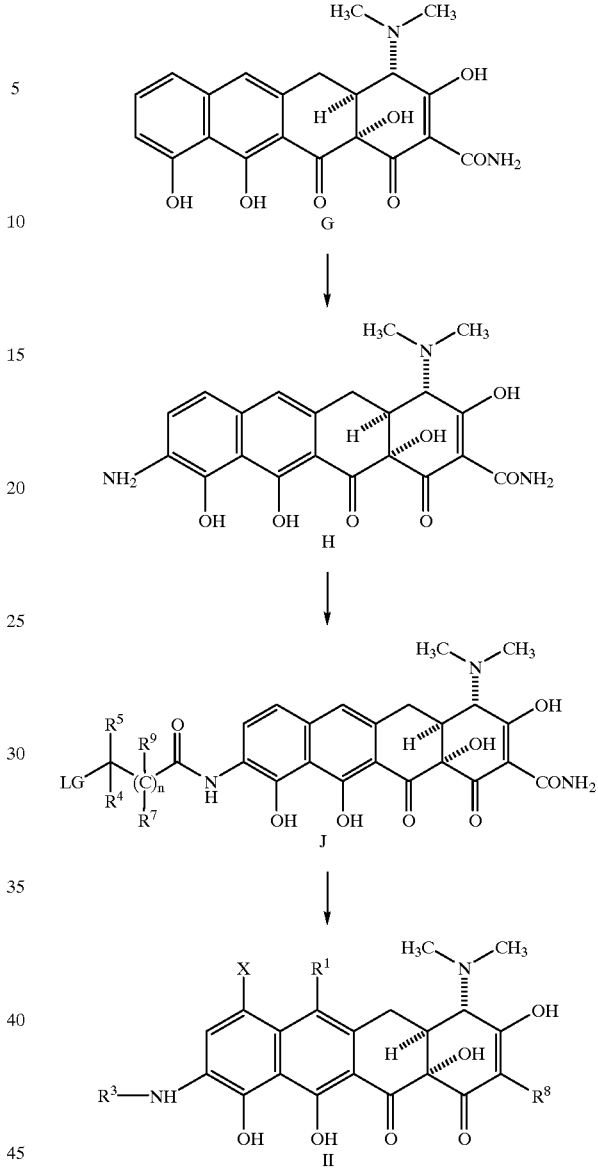

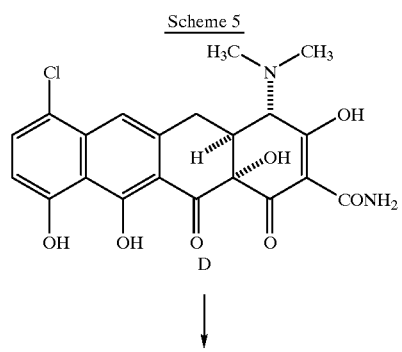

Scheme 1 refers to the preparation of compounds of the formula I wherein $R^3$ is a group of the formula $$R^5-\underset{\underset{R^4}{|}}{\overset{\overset{R^6}{|}}{C}}-(\underset{\underset{R^7}{|}}{\overset{\overset{R^9}{|}}{C}})_n-\overset{O}{\overset{||}{C}}-\xi$$

X is hydrogen, and $R^1$ is methyl.

Referring to Scheme 1, the compounds of formula I can be prepared from a compound of formula M by reduction in a reaction inert solvent. This reduction can be mediated either by transition metals or other metal reducing agents. When a transition metal mediates the reduction, a hydrogen source is also used. Suitable transition metals include palladium on carbon, palladium hydroxide on carbon, platinum oxide and platinum on activated carbon. Platinium oxide is preferred. Suitable hydrogen sources include hydrogen gas, ammonium formate and formic acid. Hydrogen gas at a pressure of about one to about three atmospheres (approximately 50 psi) is the preferred hydrogen source. Three atmospheres of hydrogen gas is the preferred pressure. Suitable solvents include ($C_1$ to $C_4$) alcohols, acetonitrile, N,N-dimethylformamide, N-methylpyrrolidinone and dilute aqueous acids such as hydrochloric or sulfuric acid. Methanol is the preferred solvent. The reaction time is one to four hours, preferably two hours. Other metal reducing agents include iron sulfate ($FeSO_4$), zinc (Zn) (metal) in glacial acetic acid, magnesium (Mg) in methanol and Zn (metal) in aqueous hydrochloric acid. Suitable solvents include excess of the solvent used to suspend the metal reducing agent, such as glacial acetic acid, ethanol and aqueous hydrochloric acid. All of the above reduction reactions are usually conducted at a temperature from about 25° C. to about 100° C., preferably about 25° C.

The compound of the formula M can be formed by reaction of a compound of the formula L with an amine reagent, wherein the amine reagent is an amine group as described above as the substituent $R^6$. Suitable solvents include ($C_1$ to $C_4$) alcohols, dimethyl sulfoxide, N,N-dimethylformamide, N-methylpyrrolidinone, acetonitrile, water, and acetone and mixtures of these solvents. Acetonitrile/N-methylpyrrolidinone (1:1) or water mixtures are the preferred solvents. Optionally, the reaction may be run in the presence of a base, preferably 4 to 20 equivalents of the amine reagent, most preferably 4 equivalents of the amine reagent. A base other than the amine reagent may be used in the reaction, suitable bases include sodium hydroxide, potassium hydroxide, triethylamine, sodium carbonate, cesium carbonate, and sodium hydrogen carbonate. The amine reagent is the preferred base. The reaction is usually conducted at a temperature of about 20° C. to about 50° C., preferably at about 25° C. The reaction time is about 5 minutes to about 30 minutes, preferably 15 minutes.

The compound of formula L may be prepared by reduction of a peroxide of the formula K. This reduction can be mediated either by transition metals or other metal reducing agents. When a transition metal mediates the reduction, a hydrogen source is also used. Suitable transition metals include palladium on carbon, palladium hydroxide on carbon, rhodium on carbon, platinum on activated carbon and platinum oxide. Five percent rhodium on carbon is preferred. Suitable hydrogen sources include hydrogen gas, ammonium formate and formic acid. Hydrogen gas at a pressure of about one to about three atmospheres is the preferred hydrogen source. Three atmospheres of hydrogen gas (approximately 50 psi) is the preferred pressure. Suitable solvents include ($C_1$ to $C_4$) alcohols, acetonitrile, N-N-dimethylformamide and N-methylpyrrolidinone. Methanol is the preferred solvent. The reaction time is about 5 to about 15 minutes, preferably about 5 minutes. Other peroxide reducing agents include sodium dithionite ($Na_2S_2O_4$), and sodium bisulfite. Suitable solvents for these other peroxide reducing reactions include water, lower alcohols such as methanol and ethanol, water and mixtures thereof. All of the above reduction reactions are usually conducted at a temperature of from about 25° C. to about 100° C., preferably about 25° C. to about 50° C. It should be noted that compounds of formula L often can be used directly from the reduction reaction without chromatographic purification.

The peroxides of formula K may be prepared by reaction of a compound of the formula B with singlet oxygen in a reaction inert solvent. The reaction is facilitated by a sensitizer such as Rose Bengal, methylene blue, or 5, 10, 15 20-tetraphenyl-21 H, 23 H-porphine (TPP), preferably 5, 10, 15, 20-tetraphenyl-21H, 23H-porphine. Singlet oxygen is produced by passing oxygen gas through the reaction mixture while the reaction mixture is irradiated with visible light with an intensity from about 300 Watts to about 600 Watts, preferably about 450 Watts. Suitable solvents for the aforesaid process include ($C_1$–$C_4$) alcohols, methylene chloride, and chloroform, and mixtures thereof. Preferably the solvent is a mixture of chloroform/methanol (25:1). The reaction is usually conducted at a temperature from about 0° C. to about 50° C., preferably at about 25° C. The reaction time is usually about 10 minutes to about 1 hour, preferably about 15 minutes.

Compounds of the formula B which is the starting material for the processes of Scheme 1 can be prepared by the methods of Scheme 3.

Scheme 2 refers to the preparation of compounds of the formula I wherein $R^3$ is a group of the formula

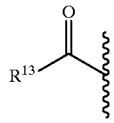

wherein X is hydrogen, and $R^1$ is methyl.

Referring to Scheme 2, the compounds of formula I can be prepared from a compound of formula P by reduction in a reaction inert solvent. This reduction can be mediated either by transition metals or other metal reducing agents. When a transition metal mediates the reduction, a hydrogen source is also used. Suitable transition metals include palladium on carbon, palladium hydroxide on carbon, rhodium on carbon, and platinum on activated carbon and platinum oxide. Platinum oxide is the preferred transition metal. Suitable hydrogen sources include hydrogen gas, ammonium formate and formic acid. Hydrogen gas at a pressure of about one to about three atmospheres is the preferred hydrogen source. Three atmospheres of hydrogen gas (approximately 50 psi) is the preferred pressure. Suitable solvents include ($C_1$ to $C_4$) alcohols, acetonitrile, N,N-dimethylformamide and N-methylpyrrolidone. Methanol is the preferred solvent. The reaction time is about 1 to about 5 hours, preferably about 2 hours. Other metal reducing agents include zinc (Zn) (metal) in glacial acetic acid, magnesium (Mg) in methanol and Zn (metal) in aqueous hydrochloric acid. Zinc metal is the preferred reducing agent of this group. Suitable solvents include excess of the solvent used to suspend the metal reducing agent, such as glacial acetic acid, methanol and aqueous hydrochloric acid. All of the above reduction reactions are usually conducted at a temperature of from about 25° C. to about 100° C., preferably about 25° C. to about 50° C.

The compounds of the formula P may be prepared by reaction of a compound of the formula O with singlet oxygen in a reaction inert solvent according to the methods described in Scheme 1 for the preparation of compounds of the formula K.

The compounds of the formula O can be prepared from a compound of the formula A by reaction with a group of the formula

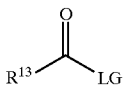

wherein LG is a leaving group such as chloro, bromo, iodo, —OSO$_2$Ph, —OSO$_2$PhCH$_3$, —OSO$_2$CH$_3$, or —OSO$_2$CF$_3$ is an inert solvent in the presence of base. Alternatively, LG can form a mixed anhydride group of the formula

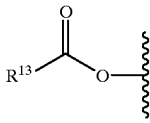

such as acetic anhydride. The preferred leaving group is chloro. Suitable solvents include dimethyl sulfoxide, N,N-dimethylformamide, N-methylpyrrolidinone, acetonitrile, and acetone. N-methylpyrrolidinone is the preferred solvent. Suitable bases include sodium hydroxide, potassium hydroxide, triethylamine, sodium carbonate, cesium carbonate, and sodium hydrogen carbonate. Sodium hydrogen carbonate is the preferred base. The reaction is usually conducted at a temperature of about 20° C. to about 50° C., preferably at about 25° C.

Compounds of the formula A which is the starting material for the processes of Scheme 2 can be prepared by the methods detailed in M. Menachery and M. Cava., "Amino Derivatives of Anhydrotetracyclines", Can. J. Chem., 62, 2583–2584 (1984).

Scheme 3 refers to the preparation of compounds of the formula II wherein X is hydrogen and R$^1$ is methyl.

Referring to Scheme 3, the compound of the formula II can be formed by reaction of a compound of the formula B with an amine reagent, wherein the amine reagent is an amine group as described above as the substituent R$^6$. Suitable solvents include (C$_1$ to C$_4$) alcohols, dimethyl sulfoxide, N,N-dimethylformamide, N-methylpyrrolidinone, acetonitrile, water, and acetone and mixtures of these solvents. Acetonitrile/N-methylpyrrolidinone (1:1) or water mixtures are the preferred solvents. Optionally, the reaction may be run in the presence of a base, preferably 4 to 20 equivalents of the amine reagent, most preferably 4 equivalents of the amine reagent. A base other than the amine reagent may be used in the reaction, suitable bases include sodium hydroxide, potassium hydroxide, triethylamine, sodium carbonate, cesium carbonate, and sodium hydrogen carbonate. The amine reagent is the preferred base. The reaction is usually conducted at a temperature of about 20° C. to about 50° C., preferably at about 25° C.

Compounds of the formula B can be prepared from a compound of formula A by reaction with a compound of formula

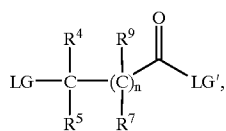

wherein LG and LG' are each independently selected from a leaving group such as chloro, bromo, iodo, —OSO$_2$Ph, —OSO$_2$PhCH$_3$, —OSO$_2$CH$_3$, or —OSO$_2$CF$_3$, in an inert solvent in the presence of base. The preferred leaving group for both LG and LG' is bromo. Suitable solvents include dimethyl sulfoxide, N,N-dimethylformamide, N-methylpyrrolidinone, acetonitrile, and acetone. N-methylpyrrolidinone is the preferred solvent. Suitable bases include sodium hydroxide, potassium hydroxide, triethylamine, sodium carbonate, cesium carbonate, and sodium hydrogen carbonate. Sodium hydrogen carbonate is the preferred base. The reaction is usually conducted at a temperature of about 10° C. to about 100° C., preferably at about 25° C.

Compounds of the formula II wherein R$^3$ is a group of the formula

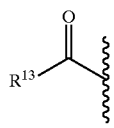

are compounds of the formula O in Scheme 2.

The compound of the formula A which is the starting material for the processes of Scheme 2 can be prepared by the methods detailed in M. Menachery and M. Cava., "Amino Derivatives of Anhydrotetracyclines", Can. J. Chem., 62, 2583–2584 (1984).

Scheme 4 refers to the preparation of compounds of the formula II wherein X is chloro and R$^1$ is hydrogen.

Referring to Scheme 4, the compound of the formula II can be prepared by reaction of a compound of the formula F with an amine reagent, wherein the amine reagent is an amine group as described above as the substituent R$^6$. Suitable solvents include (C$_1$ to C$_4$) alcohols, dimethyl sulfoxide, N,N-dimethylformamide, N-methylpyrrolidinone, acetonitrile, water, and acetone and mixtures of these solvents. Acetonitrile/N-methylpyrrolidinone (1:1) or water mixtures are the preferred solvents. Optionally, the reaction may be run in the presence of a base, preferably 4 to 20 equivalents of the amine reagent, most preferably 4 equivalents of the amine reagent. A base other than the amine reagent may be used in the reaction, suitable bases include sodium hydroxide, potassium hydroxide, triethylamine, sodium carbonate, cesium carbonate, and sodium hydrogen carbonate. The amine reagent is the preferred base. The reaction is usually conducted at a temperature of about 20° C. to about 50° C., preferably at about 25° C.

Alternatively, compounds of the formula II wherein R$^3$ is a group of the formula

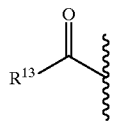

and X is chloro and R$^1$ is hydrogen, can be prepared from compounds of the formula E according to the methods described above in Scheme 2 for the preparation of compounds of the formula O from compounds of the formula A.

Compounds of the formula F can be prepared from a compound of formula E by reaction with a compound of formula

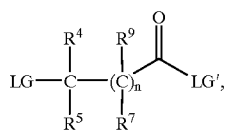

wherein LG and LG' are each independently selected from $S_N2$ leaving group such as chloro, bromo, iodo, —OSO$_2$Ph, —OSO$_2$PhCH$_3$, —OSO$_2$CH$_3$, or —OSO$_2$CF$_3$, in an inert solvent in the presence of base. The preferred leaving group is bromo. Suitable solvents include dimethyl sulfoxide, N,N-dimethylformamide, N-methylpyrrolidinone, acetonitrile, and acetone. N-methylpyrrolidinone is the preferred solvent. Suitable bases include sodium hydroxide, potassium hydroxide, triethylamine, sodium carbonate, cesium carbonate, and sodium hydrogen carbonate. Sodium hydrogen carbonate is the preferred base. The reaction is usually conducted at a temperature of about 10° C. to about 100° C., preferably at about 25° C.

An amine compound of the formula E can be prepared in two steps from a compound of the formula D. In the first step, the compound of the formula D is transformed into a nitroso intermediate by nitrosation with nitrous acid in an inert solvent. Suitable solvents include aqueous acid solution, such as aqueous hydrochloric, acetic acid, or aqueous sulfuric acid. Nitrous acid is prepared in situ according to methods well known to those of ordinary skill in the art. Preferably, sodium nitrite is dissolved in an aqueous acid solution, such as aqueous hydrochloric, acetic acid, or aqueous sulfuric acid. Aqueous hydrochloric acid is the preferable solvent. The temperature of the reaction may be in the range from about 0° C. to about 50° C., preferably about 10° C.

The nitroso intermediate is then reduced to the amine of formula E by reaction with a reducing agent in a reaction inert solvent. Suitable reducing agents include sodium dithionite in aqueous base, iron in glacial acetic acid, and zinc in acetic acid. One to about ten equivalents of the reducing agent can be used in the reaction. Preferably, 5 equivalents of the reducing agent is used. The preferred reducing agent is sodium dithionite. When sodium dithionite is the reducing agent, a base must be employed. Suitable bases include sodium hydroxide, potassium hydroxide and ammonium hydroxide. Preferably, the base is sodium hydroxide. The pH of the reduction when sodium dithionite is employed as the reducing agent is in the range of about 8 to about 12, preferably about 9. The reaction time is about 15 minutes to about 45 minutes, preferably about 30 minutes.

The compound of the formula D can be prepared from 7-chloro-6-demethyltetracycline by treatment with a strong aqueous acid. Suitable acids include concentrated sulfuric, hydrochloric or phosphoric acids. The preferred acid is concentrated hydrochloric acid. This reaction is usually conducted at a temperature of from about 25° C. to about 100° C., preferably about 50° C. to about 70° C. The reaction time for the aforesaid reaction is in the range from about 30 minutes to about 2 hours, preferably about one hour. It should be noted that compounds of formula D often can be used directly from the reduction reaction without chromatographic purification.

7-Chloro-6-demethyltetracycline, the compound of formula C, is commercially available.

Scheme 5 refers to the preparation of compounds of the formula II wherein X is hydrogen and $R^1$ is hydrogen.

Referring to Scheme 5, compounds of the formula II can be formed by reaction of a compound of the formula J with an amine reagent according to the methods described in Scheme 3 for the preparation of compounds of the formula II from compounds of the formula B.

Alternatively, compounds of the formula II wherein $R^3$ is a group of the formula

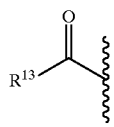

can be prepared from compounds of the formula H according to the methods of Scheme 2 for the preparation of compounds of the formula O from compounds of the formula A.

Compounds of the formula J can be prepared from a compound of formula H by reaction with a compound of formula

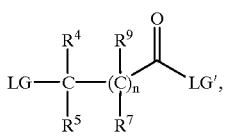

wherein LG and LG ' are each independently selected from n $S_N2$ leaving group such as chloro, bromo, iodo, —OSO$_2$Ph, —OSO$_2$PhCH$_3$, —OSO$_2$CH$_3$, or —OSO$_2$CF$_3$, in an inert solvent in the presence of base. The preferred leaving group is bromo. Suitable solvents include dimethyl sulfoxide, N,N-dimethylformamide, N-methypyrrolidinone, acetonitrile, and acetone. N-methypyrrolidinone is the preferred solvent. Suitable bases include sodium hydroxide, potassium hydroxide, triethylamine, sodium carbonate, cesium carbonate, and sodium hydrogen carbonate. Sodium hydrogen carbonate is the preferred base. The reaction is usually conducted at a temperature of about 10° C. to about 100° C., preferably at about 25° C.

The compound of the formula H can be prepared from the compound of the formula G by reaction with nitrous acid in an inert solvent according to the methods used in Scheme 4 for the preparation of the compound of the formula E from the compound of formula D.

The compound of the formula G can be prepared from the compound of the formula D by reduction in a reaction inert solvent. This reduction is mediated by transition metals in the presence of a hydrogen source. Suitable transition metals include palladium on carbon, rhodium on carbon, palladium hydroxide on carbon and platinum oxide. Ten percent palladium on carbon is preferred. Suitable hydrogen sources include hydrogen gas, ammonium formate and formic acid. Hydrogen gas at a pressure of about one to about three atmospheres is the preferred hydrogen source. Three atmospheres of hydrogen gas is the preferred pressure. Suitable solvents include ($C_1$ to $C_4$) alcohols, acetonitrile, ethyl acetate, N,N-dimethylformamide and N-methypyrrolidinone. Methanol is the preferred solvent. All of the above reduction reactions are usually conducted at a temperature of from about 25° C. to about 100° C., preferably about 25° C. The reaction time is about 30 minutes to about 2 hours, preferably about one hour. It should be noted that the compound of formula G often can be used directly from the reduction reaction without chromatographic purification.

The compound of the formula D is prepared as described in Scheme 4.

Compounds of the formula I and II wherein $R^8$ is —CONHCH$_2$—NR$^{11}$R$^{12}$ are prepared from compounds of the formula I and II wherein $R^5$ is —CONH$_2$ by reaction with formaldehyde and a compound of the formula HNR$^{11}$R$^{12}$ in a reaction inert solvent. Suitable solvents for the aforesaid process include (C$_1$ to C$_4$) alcohols, acetonitrile, ethyl acetate, N,N-dimethylformamide and N-methypyrrolidinone. t-Butyl alcohol is the preferred solvent. The aforesaid reaction is usually conducted at a temperature of from about 25° C. to about 100° C., preferably about 100° C.

Unless indicated otherwise, the pressure of each of the above reactions is not critical. Generally, the reactions will be conducted at a pressure of about one to about three atmospheres, preferably at ambient pressure (about one atmosphere).

The compounds of the formula I or II which are basic in nature are capable of forming a wide variety of different salts with various inorganic and organic acids. Although such salts must be pharmaceutically acceptable for administration to animals, it is often desirable in practice to initially isolate a compound of the formula I or II from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the free base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, e.g., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [e.g., 1,1'-methylene-bis-(2-hydroxy-3-naphthoate)] salts.

Those compounds of the formula I or II which are also acidic in nature, e.g., where $R^3$ contains a carboxylate, are capable of forming base salts with various pharmacologically acceptable cations. Examples of such salts include the alkali metal or alkaline-earth metal salts and in particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I or II. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of the reaction with maximum yields of the desired final product.

The compounds of formulae I and II of the present invention are useful in the prevention, treatment or control of bacterial infections in mammals, fish and birds. The compounds of formulae I and II exhibit broad-spectrum activity against both Gram-positive and Gram-negative aerobic and anaerobic bacteria including organisms that are resistant to tetracycline. The antibacterial activity of the compounds of the present invention against bacterial pathogens is demonstrated by the compound's ability to inhibit growth of *Pasteurella multicida*, *Pasteurella haemolytica* and *E. coli*. The following procedures are typical assays. Assay I is utilized to test for activity against tetracycline resistant or sensitive *Pasteurella multocida* and *E. coli* and Assay II is utilized to test for activity against *Pasteurella haemolytica*.

Assay I (*P. multocida* and *E. coli* assay)

This assay is based on a liquid dilution method in microtiter format. A single colony of tetracycline (tet) resistant or sensitive *P. multocida* or *E. coli* is inoculated into 5 ml of brain heart infusion (BHI) broth supplemented with tetracycline as a selective pressure (15 $\mu$g/ml and 100 $\mu$g/ml, respectively). The test compounds are prepared by solubilizing 1 mg of the compound in 125 $\mu$l of dimethylsulfoxide (DMSO). Dilutions of the test compound are prepared using uninoculated unsupplemented BHI broth with tetracycline. The concentrations of the test compound used range from 200 $\mu$g/ml to 0.098 $\mu$g/ml by two-fold serial dilutions. The *P. multocida* or *E. coli* culture is diluted with uninoculated unsupplemented BHI broth with tetracycline. This diluted cell suspensions are mixed with respective serial dilutions of the test compound to make a $10^5$/ml of final cell concentration and incubated at 37° C. for 18 hours. The minimum inhibitory concentration is equal to the concentration of the compound exhibiting 100% inhibition of growth of *P. multocida* or *E. coli* as determined by comparison with an uninoculated control.

All of the compounds of formula I and II which were tested had an MIC less than 100 $\mu$g/ml against *Pasteurella multicida* and *Pasteurella haemolytica*. All of the compounds of formula I which were tested had a MIC less that 100 $\mu$g/ml against *E. coli*.

Assay II (*P. haemolytica*)

This assay is based on an agar dilution method using a manual multiple inoculator such as a Steers Replicator®. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density (a density comparison of an unknown innoculum preparation to a standard Barium sulfate suspension). About 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula I or II can be determined by conventional animal protection studies well known to those skilled in the art. Usually these studies are carried out in mice.

Mice are allotted to cages (10 per cage) upon their arrival, and allowed to acclimate for a minimum of 48 hours before being used. Animals are inoculated with 0.5 ml of a $3\times10^3$ colony forming unit (CFU/ml bacterial suspension (*P. multocida*) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall ® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge. Surviving mice are asphyxiated with carbon dioxide at the end of the study.

The $PD_{50}$ is a calculated dose at which the compound tested protects 50% of a group of mice from mortality due to the bacterial infection which would be lethal in the absence of drug treatment.

To implement the methods of this invention for the treatment, prevention, or control of bacterial infections, an effective dose of a compound of formula I or II is administered to a susceptible or infected animal by parenteral (i.v., i.m. or s.c.), oral or topical route. The effective dose will vary with the severity of the disease, and the age, weight and condition of the animal. However, the dose will usually range from about 0.1 to about 150 mg/kg of body weight per day, preferably from about 0.1 to about 50 mg/kg.

The in vivo activity of the compounds of the invention for the treatment or prevention of osteoarthritis may be determined according to the methods of Yu et al. in *Arthritis and Rheumatism,* 34 (10), 1150–1159 (1992).

To implement the methods of this invention for the treatment or prevention of osteoarthritis, an effective dose of a compound of formula I or II is administered to a to a mammal by parenteral (i.v., I.m. or s.c.), oral, buccal or topical route. The effective dose will vary with the nature and severity of the disease, and the age, weight and condition of the animal. However, the dose will usually range from about 0.1 to about 150 mg/kg of body weight per day, preferably from about 0.1 to about 50 mg/kg. The dosage regime may be adjusted to provide the optimal therapeutic response.

This invention also provides a method of treating, preventing or controlling a bacterial infection or a mycoplasmic infection in an animal in need of such treatment, prevention or control comprising administering to said animal a bacterial or mycoplasmic effective amount of a compound of the formula (I) or (II) or a pharmaceutically acceptable salt thereof.

This invention also provides a method of treating or preventing osteoarthritis in an animal in need of such treatment or prevention comprising administering to said animal a bacterial or mycoplasmic treating amount of a compound of the formula (I) or (II) or a pharmaceutically acceptable salt thereof.

The compositions of the present invention may be formulated in a conventional manner using one or more pharmaceutically acceptable carrier. Thus, the active compounds may be formulated for oral, buccal, intranasal, parenteral (e.g., intravenous, intramuscular or subcutaneous) or rectal administration or in a form suitable for administration by inhalation or insufflation.

The active compounds may be formulated for parenteral administration by injection, including using conventional catheterization techniques or infusion. Formulations for injection may be presented in unit dosage form, e.g., in ampules or in multi-dose container, with an added preservative if needed. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle before use, e.g., sterile pyrogen-free water.

A suitable vehicle for parenterally administering either the antibiotic or osteoarthritic dose is a solution of the compound insterile water, or a solution of the compound in a solvent comprising at least 50% water and a pharmaceutically acceptable cosolvent or cosolvents such as methanol, ethanol, isopropyl alcohol, propylene glycol, glycerol, carbonate esters like diethyl carbonate, dimethyl sulfoxide, N,N-dimethylformamide, N,N-dimethylacetamide, 1-methyl-2-pyrrolidinone, and the like. Suspensions are also suitable vehicles for administering the compounds of this invention. The suspending medium can be, for example, aqueous carboxymethyl cellulose, inert oils such as peanut oil, highly refined mineral oils, aqueous polyvinylpyrrolidone and so forth. Suitable physiologically acceptable adjuvants may be necessary to maintain the compound in suspension. These adjuvants may be chosen from among thickeners such as carboxymethyl cellulose, polyvinylpyrrolidone, gelatin, and the alginates. Surfactants are also useful as suspending agents. These surfactants include; lethicin, alkyphenol polyethylene oxide adducts, naphthalenesulfonates, alkylbenzenesulfonates and polyoxyethylene sorbitan esters. Agents affecting surface tension can also help in making useful suspensions. Such agents include silicone antifoams, sorbitol, and sugars. For intravenous use the total concentration of solutes should be controlled to render the preparation isotonic. Thus in a further aspect the invention provides pharmaceutical compositions comprising a compound of the formula (I) or (II) or a pharmaceutically acceptable salt thereof together with a pharmaceutically acceptable carrier or diluent.

For oral administration, either of the osteoarthritis or antibiotic pharmaceutical compositions may take the form of, for example, tablets or capsules prepared by conventional means with pharmaceutically acceptable excipients such as binding agents (e.g., pregelantinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g. methyl or propyl p-hydroxybenzoates or sorbid acid).

For buccal administration either of the antibiotic or osteoarthritis compositions may take the form of tablets or lozenges formulated in a conventional manner.

The active compounds may also be formulated in rectal compositions such as suppositories or retention enemas, e.g., containing conventional suppository bases such as cocoa butter or other glycerides.

For intranasal administration or administration by inhalation, the active compounds are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

Typical unit dosage forms for topical administration will contain about 0.5 wt. % to about 10 wt. %, preferably about 1 wt. % to about 3.5 wt. %, most preferably about 2.5 wt. % to about 3.5 wt. % of a compound of formula I or II, based on the entire weight of the composition per topical unit dose application. If the composition is intended for sustained release such as by using microcapsules or microspheres, much larger amount of the active ingredient would of course be incorporated into an individual unit.

For topical administration, solutions or suspensions of a therapeutic agent in clear or milky lotions, gels, creams, ointments, sprays, lip balm, clothwipe, impregnated bandages and other topical and transdermal delivery devices may be employed.

Suitable solvents or vehicles, for instance, for the topical antibiotic or osteoarthritic composition of the present invention includes methanol, ethanol, propanol, acetone, n-butyl alcohol, isobutyl alcohol and the like.

The following Examples illustrate the preparation of the compounds of the present invention. Melting points are uncorrected. NMR data are reported in parts per million (δ), and are referenced to the deuterium lock signal from the sample solvent (deuterio-dimethylsulfoxide (DMSO-$d_6$) unless otherwise specified). Commercial reagents were utilized without further purification. THF refers to tetrahydrofuran. DMF refers to dimethylformamide. Preparative High Pressure Liquid Chromatography (HPLC) was carried out using reverse-phase C-8 or C-18 silica gel using the appropriate mixture of water, acetonitrile and trifluoroacetic acid. Chromatography refers to column chromatography performed using 32–63 μm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure implies the use of a rotary evaporator.

EXAMPLE 1

9-[(BROMOACETYL)AMINO] ANHYDROTETRACYCLINE

Preparation of B

9-Aminoanhydrotetracycline (prepared according to the procedure detailed in M. Menachery and M. Cava, "*Amino Derivatives of Anhydrotetracyclines*", Can. J. Chem., 62, 2583–2584 (1984)) (1.00 g, 2.09 mmol) was dissolved in 12 mol of 1-methyl-2-pyrrolidinone. Sodium bicarbonate (700 mg, 8.33 mmol) was added, followed by 220 μl of bromoacetyl bromide. The resulting reaction mixture was stirred at room temperature under an inert atmosphere of nitrogen. After 15 minutes, another 220 μl of bromoacetyl bromide was added. The resulting reaction mixture was stirred at room temperature for 90 minutes. It was then added dropwise to 300 ml of ice cold ether/isopropanol (10:1). The orange solids were collected by filtration and dried. This material was redissolved in 200 ml of water. The pH of the reaction mixture was adjusted to 5. This aqueous mixture was then extracted with ethyl acetate. The combined ethyl acetate layers were dried (sodium sulfate) and concentrated under reduced pressure to give 520 mg of the product. $^1$H NMR (dimethyl sulfoxide-$d_6$) 8.22 (d, 1H, J=9.1 Hz) 7.41 (d, 1H, J=9.1 Hz) 2.36 (s, 3H).

EXAMPLE 2

9-[(BROMOPROPIONYL)AMINO] ANHYDROTETRACYCLINE

In a procedure analogous to Example 1 except that 3-bromopropionyl-bromide was used instead of bromoacetyl bromide, the title compound was prepared.

EXAMPLE 3

9-[(PYRROLIDINOACETYL)AMINO] ANHYDROTETRACYCLINE

In a typical run, 100 mg of a compound from Example 1 was dissolved in 2 ml of anhydrous 1-methyl-2-pyrrolidinone. Pyrrolidine (0.75 ml) was added and the resulting reaction mixture was stirred at room temperature for 30 minutes. It was then added dropwise into 15 mL of ice cold ether/isopropanol (10:1). The resulting solids were collected by filtration and dried to give the desired product.

EXAMPLES 4–8

In a method analogous to Example 3 the compounds depicted in Table 1, Examples 4–8, were prepared.

EXAMPLE 9

9-(PHENYLUREA)ANHYDROTETRACYCLINE

9-Aminoanhydrotetracycline (300 mg, 0.628 mmol) was dissolved in 3 ml of 1-methyl-2-pyrrolidione. Phenyl isocyanate (112 mg, 0.942 mg) was added and the resulting reaction mixture was stirred at room temperature for 90 minutes. The reaction mixture was then added dropwise to 50 ml of ice cold ether/isopropanol (10:1). The orange solids were collected by filtration and dried to give 370 mg of the product.

EXAMPLE 10

9-[(METHOXYCARBONYL)AMINO] ANHYDROTETRACYCLINE

9-Aminoanhydrotetracycline (750 mg, 1.57 mmol) was dissolved in 5 ml of 1-methyl-2-pyrrolidinone. Sodium bicarbonate (NaHCO$_3$) (750 mg, 8.95 mmol) was added followed by 0.3 ml of methyl chloroformate. The resulting reaction mixture was stirred at room temperature for 30 min. It was then added dropwise to 30 ml of ice cold ether/isopropanol (10:1). The orange solids were collected by filtration and dried. This material was redissolved in 50 ml of water and the pH was adjusted to 5. This aqueous mixture was then extracted with ethyl acetate (EtOAc). The combined organic layers were dried over sodium sulfate (Na$_2$SO$_4$), and concentrated under reduced pressure to give 120 mg of the product.

EXAMPLES 11–13, AND 16–17

In a method analogous to Example 10 the compounds of Examples 11–13, 16 and 17, depicted in Table 1, were prepared.

EXAMPLE 14

9-(ACETYL AMINO) ANHYDROTETRACYCLINE

9-Aminoanhydrotetracycline (1.0 g, 2.09 mmol) was dissolved in 16 ml of water. Sodium acetate (0.781 g, 9.52 mmol) was added and the resulting aqueous solution was cooled to approximately 0° C. Acetic anhydride (0.30 ml) was added at 0° C. and the resulting reaction mixture was stirred at 0° C. for 20 minutes. Concentrated ammonium hydroxide (0.16 ml) was then added and the resulting reaction mixture was stirred at 0° C. for 5 minutes. The reaction mixture was warmed to room temperature and the pH was adjusted to 5 with dilute HCl. The aqueous layer was extracted with ethyl acetate. The combined organic layers were dried over sodium sulfate and concentrated under reduced pressure to give 980 mg of the title compound.

EXAMPLE 15

9-(FORMYLAMINO) ANHYDROTETRACYCLINE

9-Aminoanhydrotetracycline (500 mg, 1046 mmol) was dissolved in 8 ml of 96% formic acid along with 86 mg of sodium acetate. The reaction mixture was cooled in an ice bath and acetic anhydride (1.5 ml) was added dropwise. The resulting reaction mixture was stirred at 0° C. for 10 minutes and then at room temperature for 1 hour. The reaction mixture was then added dropwise to 50 ml of ice cold diethyl ether/isopropanol (10:1). The solids were collected by filtration and then redissolved in water. The pH was adjusted to 5 and the aqueous layer was extracted with ethyl acetate. The combined organic layers were dried over sodium sulfate and concentrated under reduced pressure to give 350 mg of the title compound.

EXAMPLE 18

9-AMINO-7-CHLORO-6-DEMETHYLANHYDROTETRACYCLINE

7-Chloro-6-demethylanhydrotetracycline (2.3 g, 4.75 mmol) was dissolved in 200 ml of water. The reaction mixture was chilled in ice and sodium nitrite was added as a solution in water (393 mg sodium nitrite in 10 ml of water). The pH of the reaction mixture was adjusted to 1 with concentrated HCl. The reaction mixture was left standing in the refrigerator (at about 15° C.) overnight. The following morning, the pH of the reaction mixture was adjusted to 9 with 5M sodium hydroxide. Sodium hydrosulfite (4.13 g) was added and the resulting reaction mixture was stirred at room temperature for 40 minutes. It was then extracted with ethyl acetate. The combined organic layers were dried (sodium sulfate), and concentrated under reduced pressure. The resulting residue was dissolved in 200 ml of methanol and 4 ml of concentrated HCl. The resulting solution was concentrated under reduced pressure to give 1.82 g of the the title compound.

EXAMPLE 19

Preparation of E

9-[(BROMOACETYL)AMINO]-7-CHLORO-6-DEMETHYLANHYDROTETRACYCLINE

In a meyhod analogous to that used in Example 1 except 9-amino-7-chloro-6-demethylanhydrotetracycline is used as a starting material 9-[{bromoacetyl}amino]-7-chloro-6-demethylanhydrotetracycline was prepared.

EXAMPLE 20

9-[(PYRROLIDINOACETYL)AMINO]-7-CHLORO-6-ANHYDROTETRACYCLINE

In a typical run, 100 mg of a compound from Example 19 was dissolved in 2 ml of anhydrous 1-methyl-2-pyrrolidinone. Pyrrolidine (0.75 ml) was added and the resulting reaction mixture was stirred at room temperature for 30 minutes. It was then added dropwise into 15 mL of ice cold ether/isopropanol (10:1). The resulting solids were collected by filtration and dried to give the desired product.

EXAMPLES 21–38

9-SUBSTITUTED-7-CHLORO-6-DEMETHYLANHYDROTETRACYCLINES

In a method analogous to that used in Example 20, using the appropriate amine reagent, the 9-substituted-7-chloro-6-demethylanhydrotetracyclines were prepared.

EXAMPLE 39

9-AMINO-6-DEMETHYLANHYDROTETRACYCLINE

7-Chloro-6-demethylanhydrotetracycline (1.5 g, 3.09 mmol) was dissolved in 20 ml of 2-methoxyethanol. The resulting solution was transferred to a hydrogenation bottle. After 460 mg of 10% palladium on carbon (Pd on C), was added, the resulting reaction mixture was hydrogenated under 50 psi of hydrogen for 5 hours. The reaction mixture was then filtered through diatomaceous earth (Celite®) to remove the catalyst. The filtrate was concentrated under reduced pressure to a volume of approximately 10 ml. This solution was then added dropwise to 100 ml of ice cold ether/isopropanol (10:1). The bright yellow solids were collected by filtration and dried to give 1.14 g of 6-demethylanhydrotetracycline.

6-Demethylanhydrotetracycline (50 mg, 1.21 mmol) was dissolved in 40 ml of water. The aqueous solution was cooled in an ice bath and sodium nitrite (100 mg, 1.45 mmol) was added as a solution in 5 ml of water. The pH of the reaction mixture was adjusted to 1 with concentrated hydrochloric acid. The resulting reaction mixture was placed in the refrigeration (about 15° C.) overnight. The following morning, the pH of the reaction mixture was adjusted to about 9 with 5 M sodium hydroxide (aq). An excess of sodium dithionite (1.05, 6.05 mmol) was added the resulting reaction mixture was stirred at room temperature for 30 minutes. (The pH was about 4.5). The aqueous layer was then extracted with ethyl acetate. The combined organic layers were dried (sodium sulfate), and concentrated under reduced pressure. The resulting residue was redissolved in 10 ml of methanol and 1 ml of concentrated hydrochloric acid. This solution was concentrated under reduced pressure and dried under high vacuum to give 148 mg of 9-amino-6-demethylanhydrotetracycline.

EXAMPLE 40

9-[(BROMOACETYL)AMINO-6-DEMETHYLANHYDROTETRACYCLINE

9-Amino-6-demethylanhydrotetracycline (178 mg, 0.383 mmol) was dissolved 2 ml of 1-methyl-2-pyrrolidone along with 168 mg of sodium bicarbonate. Bromoacetyl bromide (0.04 ml, 0.460 mmol) was added at room temperature. The resulting reaction mixture was stirred at room temperature for 30 minutes. Another portion of bromoacetyl bromide (0.022 ml, 0.249 mmol) was added and the resulting reaction mixture was stirred at room temperature for another 2 hours. The reaction mixture was then diluted with 2 ml of methanol and filtered to remove the sodium bicarbonate$_3$. The filtrate was concentrated and then added dropwise to 10 ml of ice-cold ether/isopropanol (10:1). The solids were collected by filtration and dried to give 200 mg of the crude product.

EXAMPLE 41

9-[(METHOXYCARBONYL)AMINO] TETRACYCLINE

In a typical case, 180 mg of compound from Example 10 was dissolved in 30 ml of CHCl$_3$, and 1 ml of methanol. 5, 10, 15, 20-Tetraphenyl-21H, 23H-porphine (TPP, 10 mg) was added and the resulting reaction mixture was transferred to a Pyrex round-bottom flask that was equipped with an oxygen gas inlet and vent. This Pyrex flask was placed 2–3 inches from a 450-watt, medium-pressure, mercury vapor lamp from Ace-Hanovia. This lamp, in turn, was positioned vertically inside a borosilicate photochemical immersion well that was equipped with a Pyrex absorption sleeve. The immersion well was cooled with running tap water; and the extra voltage that was required for the lamp was provided by a power supply box from Ace-Hanovia. This entire set up was placed inside the appropriate photochemical chamber. To initate the singlet oxygen photooxidation, oxygen was bubbled through the reaction mixture while it was irradiated with the 450-watt mercury vapor lamp. After 15 minutes, the lamp was turned off and the oxygen was disconnected. The reaction mixture was concentrated under reduced pressure. The resulting residue was taken up in 20 ml of methanol and filtered to remove the TPP. The filtrate, containing the peroxide intermediate was used for the next step without further purification.

The peroxide intermediate prepared above, was placed in a hydrogenation bottle. Platinum oxide (36 mg) was added and the resulting reaction mixture was hydrogenated under 50 psi of hydrogen for 2 hours. The reaction mixture was then filtered through Celite® to remove the catalyst and the filtrate was concentrated under reduced pressure. The resulting residue was redissolved in 2 ml of methanol and then added dropwise to 15 ml of ice cold ether/isopropanol (10:1). The light tan solids were collected by filtration and dried to give 70 mg of the product.

$^1$H NMR (dimethyl sulfoxide-d$_6$): 7.85 (d, 1H, J:8.4 Hz); 7.10 (d, 1H, J:8.4 Hz); 1.51 (s, 3H).

MS (LSIMS, m+1) 518.

EXAMPLE 42–45

In a method analogous to Example 41, except that the compounds prepared in Examples 10, 11, 12, 14 and 15 were respectively used instead, the 9-substituted tetracyclines were prepared.

EXAMPLE 46

9-[(N,N-DIMETHYLAMINO ACETYL)AMINO] TETRACYCLINE

In a typical run, 500 mg of the anhydrotetracycline intermediate B (Example 1) was dissolved in 50 mL of CHCl$_3$ and 2 ml of methanol. 5, 10, 15, 20-Tetraphenyl-21H, 23H-porphine (TPP, 10 mg) was added and the resulting reaction mixture was transferred to a Pyrex round-bottom flask that was equipped with an oxygen gas inlet and vent. This Pyrex flask was placed 2–3 inches from a 450-watt, medium-pressure, mercury vapor lamp from Ace-Hanovia. This lamp, in turn, was positioned vertically inside a borosilicate photochemical immersion well that was equipped with a Pyrex absorption sleeve. The immersion well was cooled with running tap water; and the extra voltage that was required for the lamp was provided by a power supply box from Ace-Hanovia. This entire set up was placed inside the appropriate photochemical chamber. To initate the singlet oxygen photooxidation, oxygen was bubled through the reaction mixture while it was irradiated with the 450-watt mercury vapor lamp. After 15 minutes, the lamp was turned off and the oxygen was disconnected. The reaction mixture was concentrated under reduced pressure. The resulting residue was taken up in 30 ml of methanol and filtered to remove the TPP. The filtrate, containing the peroxide intermediate was used for the next step without further purification.

$^1$H NMR (dimethyl sulfoxide-d$_6$) 8.26 (d, 1H, J=8.9 Hz), 7.24 (d, 1H, J=8.9 Hz), 1.55 (s, 3H).

The peroxide intermediate, prepared above, was transferred to a hydrogenation bottle. 5% Rhodium on carbon (120 mg) was added and the resulting reaction mixture was hydrogenated under 50 psi of hydrogen for 5 minutes at room temperature. The reaction mixture was filtered through diatomaceous earth to remove the catalyst. The filtrate was concentrated under reduced pressure to give 380 mg of 9-[(bromoacetyl)-amino]dehydrotetracycline.

$^1$H NMR (dimethyl sulfoxide-d$_6$) 8.26 (d, 1H, J=8.2 Hz), 7.24 (d, 1H, J=8.2 Hz), 1.55 (s, 3H).

9-[(Bromoacetyl)amino]dehydrotetracycline (320 mg) was dissolved in 4 ml of the 40% solution of dimethylamine in water and 1 mL of methanol. The resulting reaction mixture was stirred at room temperature for 30 minutes. The reaction mixture was then concentrated under reduced pressure. The resulting residue was redissolved in 5 ml of methanol and added dropwise to 30 ml of ice cold ether/isopropanol (10:1). The brown solids were collected by filtration and dried to give 319 mg of the free base of the dehydrotetracycline.

$^1$H NMR (dimethyl sulfoxide-d$_6$) 8.17 (d, 1H, J=8.3 Hz), 6.85 (d, 1H, J=8.3 Hz), 1.37 (s, 3H). MS (LSIMS, m+1)= 543.

This material was converted to the hydrochloride salt by dissolution in 10 ml of methanol followed by addition of 2 equivalents of 1N aqueous hydrochloric acid.

¹H NMR (dimethyl sulfoxide-d₆) 8.10 (d, 1H, J=8.3 Hz), 7.32 (d, 1H, J=8.3 Hz), 1.60 (s, 3H).

The solution containing the hydrochloride salt of the dehydrotetracycline (prepared above) was transferred to a hydrogenation bottle. Platinum oxide (52 mg) was added and the resulting reaction mixture was hydrogenated under 50 psi of hydrogen for 2 hours at room temperature. The reaction mixture was filtered through Celite®. The filtrate was concentrated under reduced pressure and dried under high vacuum to obtain 202 mg of the title compound.

¹H NMR (dimethyl sulfoxide-d₆) 8.10 (d, 1H, J=8.2 Hz), 7.13 (d, 1H, J=8.2 Hz), 1.52 (s, 3H). MS (LSIMS, m+1)= 545. Analytically pure sample was obtained by preparative HPLC.

EXAMPLE 47

9-[(t-BUTYLAMINOACETYL)AMINO] TETRACYCLINE

9-[(Bromoacetyl)amino]dehydrotetracycline, from Example 46, (340 mg, 0.604 mmol) was dissolved in 3 ml of anhydrous acetonitrile and 1 ml of 1-methyl-2-pyrrolidinone. t-Butylamine (0.25 ml, 2.42 mmol) was added and the resulting reaction mixture was stirred at room temperature for 40 minutes. The reaction mixture was concentrated under reduced pressure. The resulting residue was dissolved in 3 ml of methanol and added dropwise to 15 ml of ice cold ether/isopropanol (10:1). The brown solids were collected by filtration and dried to give 280 mg of 9-[(t-butylamino-acetyl)amino]dehydrotetracycline. Some of this material (250 mg) was converted to the hydrochloride salt by dissolving it in 10 ml of methanol followed by addition of two equivalents of 1N aqueous hydrochloric acid.

A solution containing 150 mg of the hydrochloride salt of the dehydrotetracycline in 10 ml of methanol was transferred to a hydrogenation bottle. Platinum oxide (30 mg) was added and the resulting reaction mixture was hydrogenated under 50 psi of hydrogen for 2 hours at room temperature. The reaction mixture was filtered through Celite® to remove the catalyst. The filtrate was concentrated to a volume of about 4 ml. This was then added dropwise to 15 ml of ice cold ether/isopropanol (10:1). The light tan solids were collected by filtration and dried to give 110 mg of the title compound.

¹H NMR (dimethyl sulfoxide-d₆) 8.25 (d, 1H, J=8.3 Hz), 7.18 (d, 1H, J=8.3 Hz), 1.55 (s, 3H), 1.29 (s, 9H). MS (LSIMS, m+1)=574. An analytically pure sample was obtained by preparative HPLC.

EXAMPLES 48–52 AND 54–63

In a method analogous to Example 47, except that the appropriate amine reagent was used, the 9-substituted tetracyclines of Examples 48–52 and 54–63 were prepared.

EXAMPLE 53

9-(METHYLAMINOACETYLAMINO) TETRACYCLINE

In a method analogous to Example 46 except that 40% methylamine in water was used instead of 40% dimethylamine in water, the title compound was prepared.

TABLE 1

| Example No. | R³—NH— | X | R¹ | R⁸ | MS(LSIMS) (m + 1) |
|---|---|---|---|---|---|
| 1 | Br-CH₂-C(O)-NH- | H | CH₃ | CONH₂ | (m − Br) = 482 |
| 2 | Br-(CH₂)₃-C(O)-NH- | H | CH₃ | CONH₂ | NT |
| 3 | pyrrolidinyl-CH₂-C(O)-NH- | H | CH₃ | CONH₂ | 553 |

TABLE 1-continued
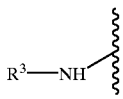
| Example No. | R³—NH 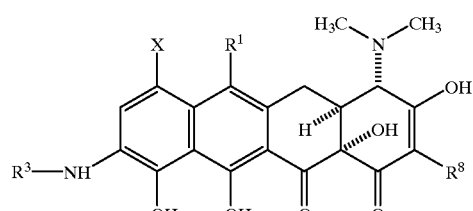 | X | R¹ | R⁸ | MS(LSIMS) (m + 1) |
|---|---|---|---|---|---|
| 4 | 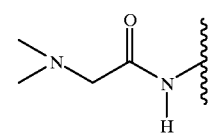 | H | CH₃ | CONH₂ | 527 |
| 5 | 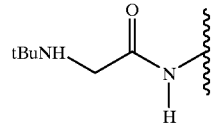 | H | CH₃ | CONH₂ | 555 |
| 6 | 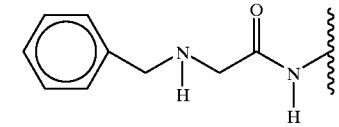 | H | CH₃ | CONH₂ | 589 |
| 7 | 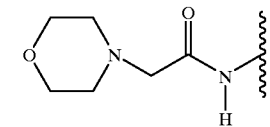 | H | CH₃ | CONH₂ | 569 |
| 8 | 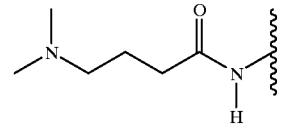 | H | CH₃ | CONH₂ | 555 |
| 9 | 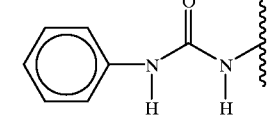 | H | CH₃ | CONH₂ | 561 |
| 10 | 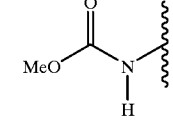 | H | CH₃ | CONH₂ | 449 |
| 11 | 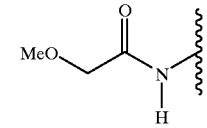 | H | CH₃ | CONH₂ | 514 |

TABLE 1-continued
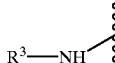
| Example No. | R³—NH— | X | R¹ | R⁸ | MS(LSIMS) (m + 1) |
|---|---|---|---|---|---|
| 12 | 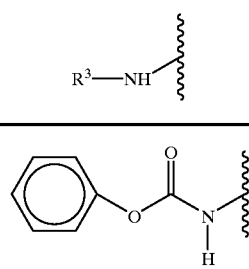 | H | $CH_3$ | $CONH_2$ | 562 |
| 13 | 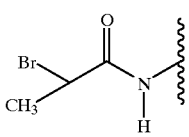 | H | $CH_3$ | $CONH_2$ | N.T. |
| 14 | 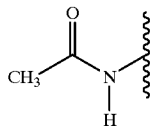 | H | $CH_3$ | $CONH_2$ | 483 |
| 15 | 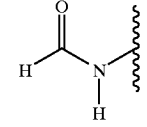 | H | $CH_3$ | $CONH_2$ | 469 |
| 16 | 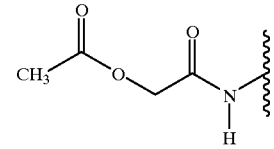 | H | $CH_3$ | $CONH_2$ | 542 |
| 17 | 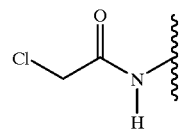 | H | $CH_3$ | $CONH_2$ | 517 |
| 18 |  | Cl | H | $CONH_2$ | 498 |
| 19 | 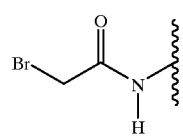 | Cl | H | $CONH_2$ | 502 (m + −Br) |

TABLE 1-continued
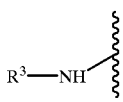
| Example No. | R³—NH | X | R¹ | R⁸ | MS(LSIMS) (m + 1) |
|---|---|---|---|---|---|
| 20 | 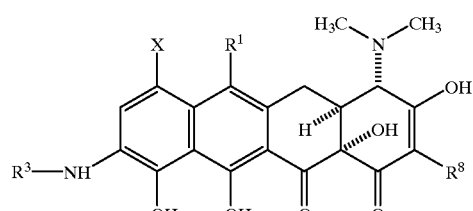 | Cl | H | $CONH_2$ | 573 |
| 21 | 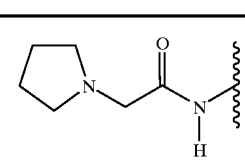 | Cl | H | $CONH_2$ | 611 |
| 22 | 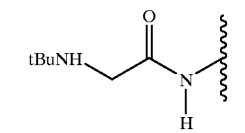 | Cl | H | $CONH_2$ | 575 |
| 23 | 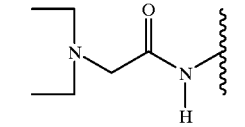 | Cl | H | $CONH_2$ | 559 |
| 24 | 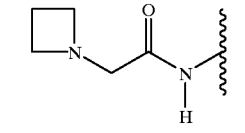 | Cl | H | $CONH_2$ | 609 |
| 25 | 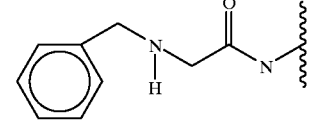 | Cl | H | $CONH_2$ | 587 |
| 26 | 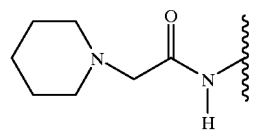 | Cl | H | $CONH_2$ | 589 |
| 27 | 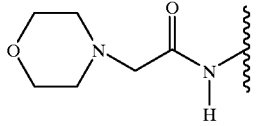 | Cl | H | $CONH_2$ | 547 |

TABLE 1-continued
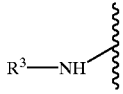
| Example No. | R³—NH 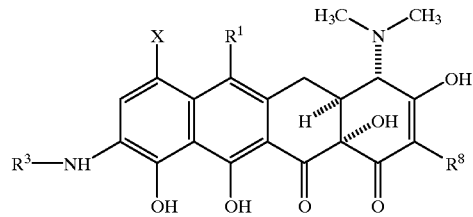 | X | R¹ | R⁸ | MS(LSIMS) (m + 1) |
|---|---|---|---|---|---|
| 28 | 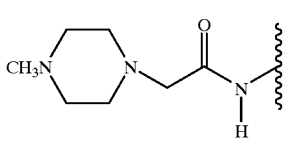 | Cl | H | $CONH_2$ | 602 |
| 29 | 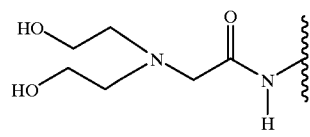 | Cl | H | $CONH_2$ | 607 |
| 30 | 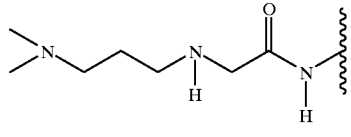 | Cl | H | $CONH_2$ | 604 |
| 31 | 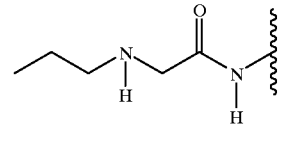 | Cl | H | $CONH_2$ | 561 |
| 32 | 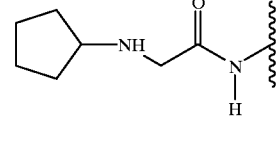 | Cl | H | $CONH_2$ | 587 |
| 33 | 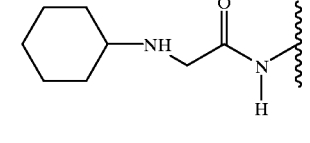 | Cl | H | $CONH_2$ | 601 |
| 34 | 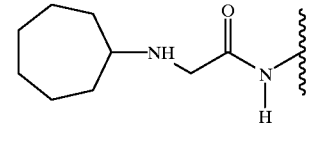 | Cl | H | $CONH_2$ | 615 |
| 35 | 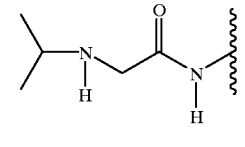 | Cl | H | $CONH_2$ | 561 |

TABLE 1-continued
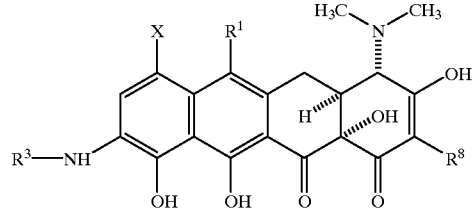
| Example No. | R³—NH— | X | R¹ | R⁸ | MS(LSIMS) (m + 1) |
|---|---|---|---|---|---|
| 36 | 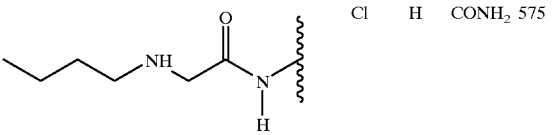 | Cl | H | $CONH_2$ | 575 |
| 37 | 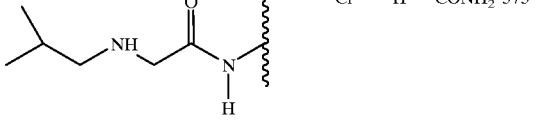 | Cl | H | $CONH_2$ | 575 |
| 38 | 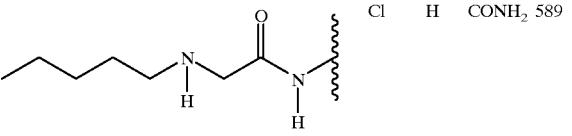 | Cl | H | $CONH_2$ | 589 |
| 39 |  | H | H | $CONH_2$ | 427 |
| 40 |  | H | H | $CONH_2$ | 467 (m + −Br) |

TABLE 2
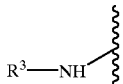
| No. | R³—NH— | X | R¹ | R⁸ | MS(LSIMS) (m + 1) |
|---|---|---|---|---|---|
| 41 | 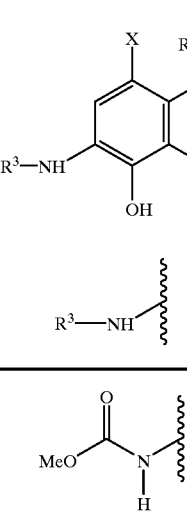 | H | CH₃ | CONH₂ | 518 |
| 42 | 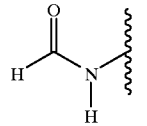 | H | CH₃ | CONH₂ | 487 |
| 43 | 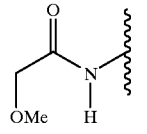 | H | CH₃ | CONH₂ | 532 |
| 44 | 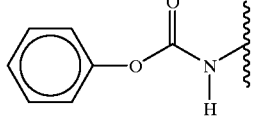 | H | CH₃ | CONH₂ | 580 |
| 45 | 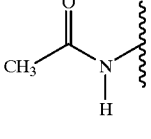 | H | CH₃ | CONH₂ | 502 |
| 46 | 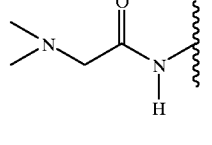 | H | CH₃ | CONH₂ | 545 |
| 47 | 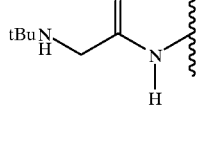 | H | CH₃ | CONH₂ | 574 |
| 48 | 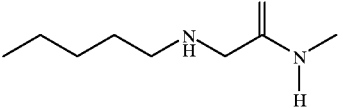 | H | CH₃ | CONH₂ | 487 |

TABLE 2-continued
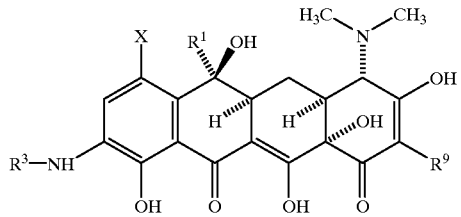
| No. | R³—NH | X | R¹ | R⁸ | MS(LSIMS) (m + 1) |
|---|---|---|---|---|---|
| 49 | 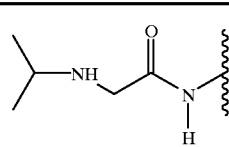 | H | CH₃ | CONH₂ | 559 |
| 50 | 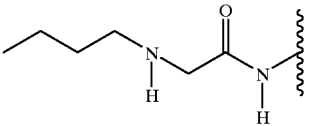 | H | CH₃ | CONH₂ | 573 |
| 51 | 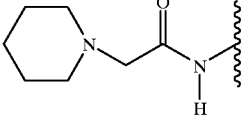 | H | CH₃ | CONH₂ | 585 |
| 52 | 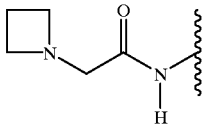 | H | CH₃ | CONH₂ | 557 |
| 53 | 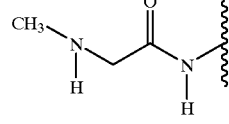 | H | CH₃ | CONH₂ | 530 |
| 54 | 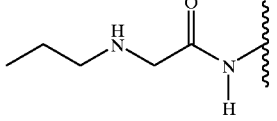 | H | CH₃ | CONH₂ | 559 |
| 55 | 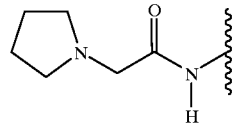 | H | CH₃ | CONH₂ | 571 |
| 56 | 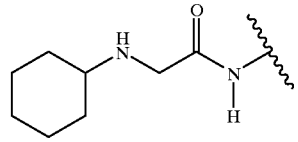 | H | CH₃ | CONH₂ | 599 |

TABLE 2-continued
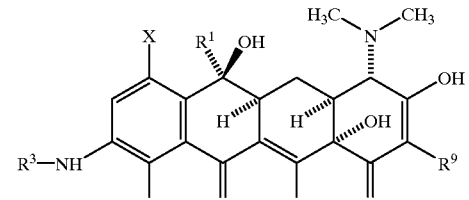
| No. | R³—NH structure | X | R¹ | R⁸ | MS(LSIMS) (m + 1) |
|---|---|---|---|---|---|
| 57 | 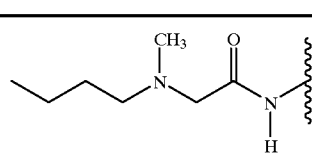 | H | $CH_3$ | $CONH_2$ | 587 |
| 58 | 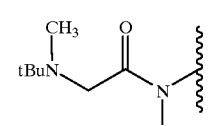 | H | $CH_3$ | $CONH_2$ | 587 |
| 59 | 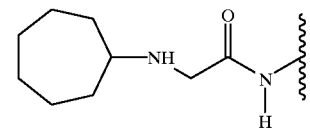 | H | $CH_3$ | $CONH_2$ | 613 |
| 60 | 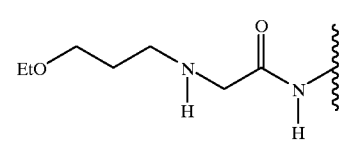 | H | $CH_3$ | $CONH_2$ | 603 |
| 61 | 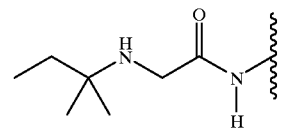 | H | $CH_3$ | $CONH_2$ | 603 |
| 62 | 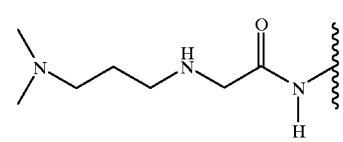 | H | $CH_3$ | $CONH_2$ | 602 |

TABLE 2-continued

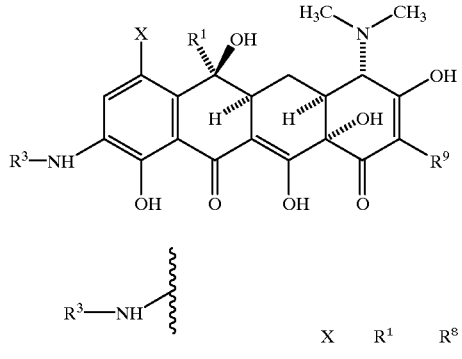

| No. | $R^3$—NH— | X | $R^1$ | $R^8$ | MS(LSIMS) (m + 1) |
|---|---|---|---|---|---|
| 63 | 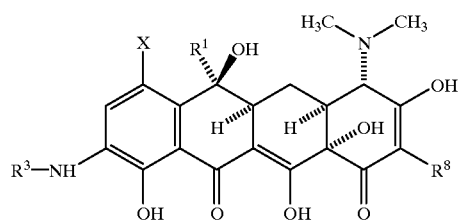 | H | $CH_3$ | $CONH_2$ | 573 |

What is claimed is:

1. A compound of the formula

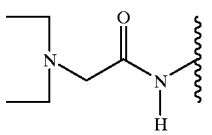   I wherein X is hydrogen;

$R^1$ is methyl;

$R^3$ is a group of the formula

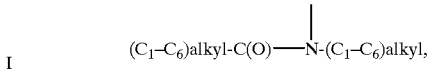

wherein n is an integer from zero to four;

$R^4$ is hydrogen or $(C_1-C_6)$alkyl;

$R^5$ is hydrogen; $(C_1-C_6)$alkyl optionally substituted with one or more substituents independently selected from methylthio, $(C_1-C_6)$alkoxy, amino, guanidino, amido, carboxamido, $(C_1-C_6)$alkyl-C(O)—O—, $(C_1-C_6)$alkyl-HN—C(O)—, di$(C_1-C_6)$alkyl-N—C(O)—, di$(C_1-C_6)$alkyl-N—C(O)—, $(C_1-C_6)$alkyl-C(O)—NH—

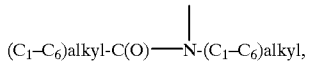

$(C_1-C_6)$alkyl-O—C(O)—, HC(O)—NH—, and HO—C(O)—; $(C_6-C_{10})$aryl-$(CH_2)_h$—, wherein h is an integer from zero to three, wherein the $(C_6-C_{10})$aryl moiety of said $(C_6-C_{10})$aryl-$(CH_2)_h$ group may optionally be substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkyl-HN—C(O)—, di$(C_1-C_6)$alkyl-N—C(O)—, $(C_1-C_6)$alkyl-C(O)—NH—,

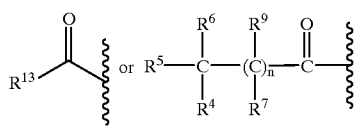

$(C_1-C_6)$alkyl-O—C(O)—, HC(O)—NH—, and HO—C(O)—; or $(C_3-C_6)$cycloalkyl-$(CH_2)_j$—, wherein j is an integer from zero to three, wherein the $(C_3-C_6)$cycloalkyl moiety of said $(C_3-C_6)$cycloalkyl-$(CH_2)_j$— group may optionally be substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

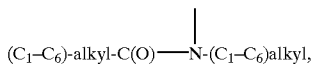

$(C_1-C_6)$alkyl-O—C(O)—, HC(O)—NH—, and HO—C(O)—;

R⁶ is halogen; amino; hydroxylamino; $(C_1-C_{12})$ alkylamino optionally substitued with one or more substituents independently selected from halogen, hydroxy, $(C_1-C_6)$alkoxy, $(C_1-C_6)$alkylsulfonyl, trihalo $(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

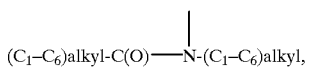

$(C_1-C_6)$alkyl-O—C(O)—, HC(O)—NH—, and HO—C(O)—; $(C_3-C_{18})$cycloalkylamino wherein the $(C_3-C_{18})$cycloalkyl moiety of said $(C_3-C_{18})$cycloalkyl amino group may optionally be substituted with one or more substituents independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl, $(C_1-C_6)$alkyl-C(O)—O—, $(C_1-C_6)$alkyl-HN—C(O)—, di$(C_1-C_6)$alkyl-N—C(O)—, $(C_1-C_6)$-alkyl-C(O)—NH—,

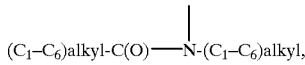

$(C_1-C_6)$alkyl-O—C(O)—, HC(O)—NH—, and HO—C(O)—; and wherein the amino moiety of said $(C_3-C_{18})$cycloalkylamino group may optionally be substituted with $(C_1-C_6)$alkyl; di$(C_3-C_{18})$cycloalkyl-amino optionally substituted with one or more substituents independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl, $(C_1-C_6)$alkyl-C(O)—O—, $(C_1-C_6)$alkyl-HN—C(O)—, di$(C_1-C_6)$alkyl-N—C(O)—, $(C_1-C_6)$-alkyl-C(O)—NH—,

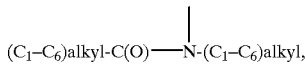

$(C_1-C_6)$alkyl-O—C(O)—, HC(O)—NH—, and HO—C(O)—; $(C_6-C_{10})$aryl-$(CH_2)_m$-amino, wherein m is an integer from zero to three, wherein the $(C_6-C_{10})$aryl moiety of said $(C_6-C_{10})$aryl-$(CH_{2m}$-amino group may optionally be substituted with one or more substituents independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl, $(C_1-C_6)$alkyl-C(O)—O—, $(C_1-C_6)$alkyl-HN—C(O)—, di$(C_1-C_6)$alkyl-N—C(O)—, $(C_1-C_6)$-alkyl-C(O)—NH—, $(C_1-C_6)$alkyl-C(O)—N—$(C_1-C_6)$alkyl, $(C_1-C_6)$alkyl-O—C(O)—, HC(O)—NH—, and HO—C(O)—; di$(C_1-C_8)$alkyl-amino optionally substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

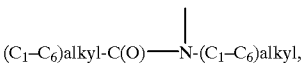

$(C_1-C_6)$alkyl-O—C(O)—, HC(O)—NH—, and HO—C(O)—; $(C_2-C_{10})$azacycloalkyl optionally substituted with one or more substituents independently selected from halogen, hydroxy, $(C_1-C_6)$alkyl, $(C_1-C_6)$alkoxy, $(C_{1-C6})$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

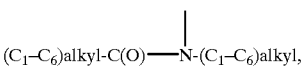

$(C_1-C_6)$alkyl-O—C(O)—, HC(O)—NH—, and HO—C(O)—; carboxy$(C_1-C_6)$alkylamino; $(C_1-C_6)$alkyl-O—C(O)-amino; $(C_1-C_6)$alkyl-O—C(O)—$(C_1-C_6)$alkylamino; $(C_1-C_6)$alkoxyamino; $(C_3-C_8)$cycloalkoxyamino; $(C_6-C_{10})$aryl-$(CH_2)_t$-oxyamino, wherein t is an integer from zero to three, wherein the $(C_6-C_{10})$aryl moiety of said $(C_6-C_{10})$aryl-$(CH_2)_t$-oxyamino group may optionally be substituted with one or more substituents independently selected from halogen, $(C_1-C_6)$alkoxy, trihalo$(C_1-C_6)$alkyl, amino, cyano, $(C_1-C_6)$alkylamino, hydroxy, $(C_1-C_6)$alkyl, $(C_1-C_6)$alkylsulfonyl, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

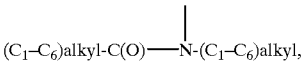

$(C_1-C_6)$alkyl-O—(O)—, HC(O)—NH—, and HO—C(O)—; or a heterocycle-$(CH_2)_k$-amino group, wherein k is an integer from zero to three, wherein said heterocycle is selected from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein the heterocycle moiety of said heterocycle-$(CH_2)_k$—group may be, where possible, substituted with from one to three substituents independently selected from $(C_1-C_6)$alkyl, halogen, hydroxy, cyano, $(C_1-C_6)$alkoxy, $(C_1-C_6$alkylsulfonyl, trihalo$(C_1-C_6)$alkyl, amino, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

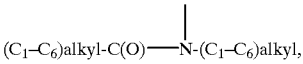

$(C_1-C_6)$alkyl-O—C(O)—, HC(O)—NH—, and HO—(O)—; or R⁵ and R⁶ taken together may form a —$(CH_2)_p W(CH_2)_q$—ring wherein W is selected from

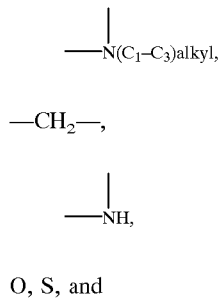

—CH$_2$—,

O, S, and

wherein B is selected from hydrogen and (C$_1$—C$_3$)alkyl, p is an integer from one to three, and q is an integer from one to three;

R$^7$ is hydrogen or (C$_1$–C$_6$) alkyl;

R$^8$ is —CONH$_2$ or —CONHCH$_2$-NR$^{11}$R$^{12}$;

R$^9$ is hydrogen or (C$_1$–C$_6$)alkyl;

R$^{11}$ is (C$_1$–C$_6$)alkyl;

R$^{12}$ is (C$_1$–C$_6$)alkyl; or

R$^{11}$ and R$^{12}$ taken together form a —(CH$_2$)$_r$—Y—(CH$_2$)$_s$ ring wherein Y is

—CH$_2$—,

oxygen, sulfur or —NOB; wherein B is selected from hydrogen and (C$_1$–C$_3$)alkyl, r is an integer from one to three, and s is an integer from one to three;

R$^{13}$ is hydrogen, (C$_1$–C$_6$)alkoxy-(C$_1$–C$_6$)alkyl, (C$_1$–C$_6$) alkyl, (C$_1$–C$_6$) alkoxy, (C$_3$–C$_6$)cycloalkyl, (C$_3$–C$_6$) cycloalkylmethyl, or (C$_6$–C$_{10}$)aryl optionally substituted with one or more substituents independently selected from fluoro, hydroxy, (C$_1$–C$_6$)alkoxy, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$) alkyl-C(O)—O—, (C$_1$–C$_6$)alkyl-HN-C(O)—, di(C$_1$–C$_6$)alkyl-N-C(O)—, (C$_1$–C$_6$)alkyl-C(O)—NH—,

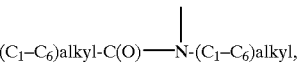

(C$_1$–C$_6$)alkyl-O—C(O)—, HC(O)—NH—, and HO—C(O)—; and the pharmacologically acceptable organic and inorganic salts or metal complexes.

2. A compound according to claim 1 wherein X is hydrogen, R$^1$ is methyl, and R$^8$ is —CONH$_2$.

3. A compound according to claim 2 wherein n is zero; R$^4$ is hydrogen; and R$^5$ is hydrogen.

4. A compound according to claim 3 wherein R$^6$ is halogen, amino, hydroxylamino, (C$_1$–C$_{12}$)alkylamino optionally substitued with one or more substituents independently selected from halogen, hydroxy, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

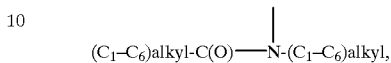

(C$_1$–C$_6$)alkyl-O—C(O)—, HC(O)—NH—, and HO—C(O)—; (C$_3$–C$_{18}$)cycloalkylamino wherein the (C$_3$–C$_{18}$)cycloalkyl moiety of said (C$_3$–C$_{18}$)cycloalkyl amino group may optionally be substituted with one or more substituents independently selected from halogen, hydroxy, (C$_1$–C$_6$) alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

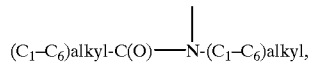

(C$_1$–C$_6$alkyl-O—C(O)—, HC(O)—NH—, and HO—C(O)—; and wherein the amino moiety of said C$_3$–C$_{18}$) cycloalkyl amino group may optionally be substituted with (C$_1$–C$_6$)alkyl; di(C$_1$–C$_8$)alkyl-amino optionally substituted with one or more substituents independently selected from halogen, hydroxy, (C$_1$–C$_6$)alkyl, (C$_1$–C$_6$)alkoxy, (C$_1$–C$_6$) alkylsulfonyl, trihalo(C$_1$–C$_6$)alkyl, amino, cyano, (C$_1$–C$_6$) alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

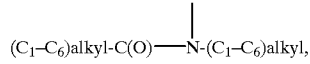

(C$_1$–C$_6$)alkyl-O—C(O)—, HC(O)—NH—, and HO—C(O)—; (C$_2$–C$_{10}$)azacycloalkyl optionally substituted with one or more substitutents independently selected from halogen, hydroxy, (C$_1$–C$_6$)alkyl, (C$_1$–C$_6$)alkoxy, (C$_1$–C$_6$) alkylsulfonyl, trihalo(C$_1$–C$_6$)alkyl, amino, cyano, (C$_1$–C$_6$) alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

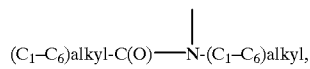

(C$_1$–C$_6$)alkyl-O—C(O)—, HC(O)—NH—, and HO—C(O)—; or R$^5$ and R$^6$ taken together may form a —(CH$_2$)$_p$W(CH$_2$)$_q$— ring wherein A is selected from

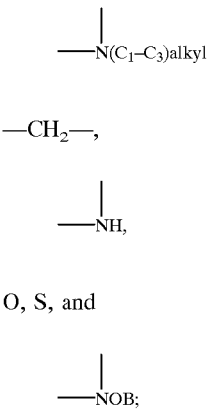

wherein B is selected from hydrogen and $(C_1-C_3)$alkyl, p is an integer from one to three, and q is an integer from one to three.

5. A compound according to claim 4 wherein said compound is selected from:

9-[(N,N-dimethylaminoacetyl)amino]tetracycline;
9-[(tert-butylaminoacetyl)amino]tetracycline;
9-[(N-methyl-N'-tert-butylaminoacetyl)amino]tetracycline;
9-[(diisoproplaminoacetyl)amino]tetracycline;
9-[(pyrrolidinoacetyl)amino]tetracycline;
9-[(cycloheptylaminoacetyl)amino]tetracycline; and
9-[(tert-amylaminoacetyl)amino]tetracycline.

6. A compound of the formula

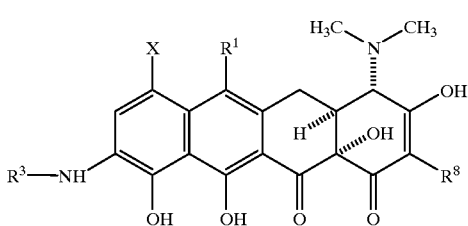

II wherein X is hydrogen or chlorine;
$R^1$ is H or $CH_3$;
$R^3$ is a group of the formula

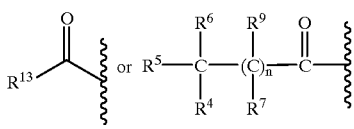

wherein n is an integer from zero to four;
$R^4$ is hydrogen or $(C_1-C_6)$alkyl;
$R^5$ is hydrogen; $(C_1-C_6)$alkyl optionally substituted with one or more substituents independently selected from methylthio, $(C_1-C_6)$alkoxy, amino, guanidino, amido, carboxamido, $(C_1-C_6)$alkyl-C(O)—O—, $(C_1-C_6)$ alkyl-HN—C(O)—, di$(C_1-C_6)$alkyl-N—C(O)—, $(C_1-C_6)$alkyl-C(O)—NH—, $(C_1-C_6)$alkyl-C(O)—N(C_1-C_6)$alkyl, $(C_1-C_6)$alkyl-O—C(O)—, HC(O)—NH—, and HO—C(O)—; $(C_6-C_{10})$aryl-$(CH_2)_h$-, wherein h is an integer from zero to three, wherein the $(C_6-C_{10})$aryl moiety of said $(C_6-C_{10})$aryl-$(CH_2)_h$ group may optionally be substituted with one or more substituents independently selected from halogen, hydroxy, $(C_1-C_6)$alkyl, $(C_1-C_6)$alkoxy, $(C_1-C_6)$alkyllsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—, $(C_1-C_6)$alkyl-C(O)—N(C_1-C_6)$alkyl, $(C_1-C_6)$alkyl-O—C(O)—, HC(O)—NH—, and HO—C(O)—; or $(C_3-C_6)$cycloalkyl-$(Ch_2)_j$—, wherein j is an integer from zero to three, wherein the $(C_3-C_6)$cycloalkyl moiety of said $(C_3-C_6)$cycloalkyl-$(CH_2)_j$— group may optionallu be substituted with one or more substituents independently selected from halogen, hydroxy, $(C_1-C_6)$ alkyl, $(C_1-C_6)$alkoxy, $(C_1-C_6)$alkyllsulfonyl, trihalo$(C_1-C_6)$alkyl, amino, cyano, $(C_1-C_6)$alkylamino, di$(C_1-C_6)$ alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—, $(C_1-C_6)$alkyl-C(O)—N(C_1-C_6)$alkyl, $(C_1-C_6)$alkyl-O—C(O)—, HC(O)—NH—, and HO—C(O)—;

$R^6$ is halogen; amino; hydroxylamino; $(C_1-C_{12})$ alkylamino optionally substitued with one or more substituents independently selected from halogen, hydroxy, $(C_1-C_6)$alkoxy, $(C_1-C_6)$alkylsulfonyl, trihalo $(C_1-C_6)$alkyl, amino, cyano, $(C_1-C_6)$alkylamino, di$(C_1-C_6)$alkylamino, amido, carboxamido, $(C_1-C_6)$ alkyl-C(O)—O—, $(C_1-C_6)$alkyl-HN—C(O)—, di$(C_1-C_6)$alkyl-N—C(O)—, $(C_1-C_6)$alkyl-C(O)—NH—, $(C_1-C_6)$alkyl-C(O)—N(C_1-C_6)$alkyl, $(C_1-C_6)$alkyl-O—C(O)—, HC(O)—NH—, and HO—C(O)—; $(C_3-C_{18})$cycloalkylamino wherein the $(C_3-C_{18})$ cycloalkyl moiety of said $(C_3-C_{18})$cycloalkyl amino group may optionally be substituted with one or more substituents independently selected from halogen, hydroxy, $(C_1-C_6)$ alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl, $(C_1-C_6)$alkyl-C(O)—O—, $(C_1-C_6)$alkyl-HN—C(O)—, di$(C_1-C_6)$alkyl-N—C(O)—, $(C_1-C_6)$ alkyl-C(O)—NH—,

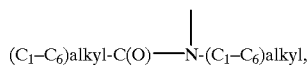

(C$_1$–C$_6$)alkyl-O—C(O)—, HC(O)—NH—, and HO—C(O)—; and wherein the amino moiety of said (C$_3$–C$_{18}$) cycloalkyl amino group may optionally be substituted with (C$_1$–C$_6$)alkyl; di(C$_3$–C$_{18}$)cycloalkyl-amino optionally substituted with one or more substituents independently selected from halogen, hydroxy, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$) alkyl-C(O)—NH—,

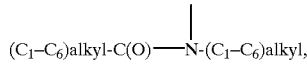

(C$_1$–C$_6$)alkyl-O—C(O)—, HC(O)—NH—, and HO—C(O)—; (C$_6$–C$_{10}$)aryl-(CH$_2$)$_m$-amino, wherein m is an integer from zero to three, wherein the (C$_6$–C$_{10}$)aryl moiety of said (C$_6$–C$_{10}$)aryl-(CH$_2$)$_m$-amino group may optionally be substituted with one or more substituents independently selected from halogen, hydroxy, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl—C(O)—NH—, (C$_1$–C$_6$)alkyl-C(O)—N—(C$_1$–C$_6$)alkyl, (C$_1$–C$_6$)alkyl-O—C(O)—, HC(O)—NH—, and HO—C(O)—; di(C$_1$–C$_8$)alkyl-amino optionally substituted with one or more substituents independently selected from halogen, hydroxy, (C$_1$–C$_6$)alkyl, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

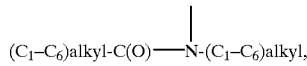

(C$_1$–C$_6$)alkyl-O—C(O)—, HC(O)—NH—, and HO—C(O)—; (C$_2$–C$_{10}$)azacycloalkyl optionally substituted with one or more substituents independently selected from halogen, hydroxy, (C$_1$–C$_6$)alkyl, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$) alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

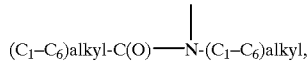

(C$_1$–C$_6$)alkyl-O—C(O)—, HC(O)—NH—, and HO—C(O)—; carboxy(C$_1$–C$_6$)alkylamino; (C$_1$–C$_6$)alkyl-O—C(O)-amino; (C$_1$–C$_6$)alkyl-O—C(O)—(C$_1$–C$_6$)alkylamino; (C$_1$–C$_6$)alkoxyamino; (C$_3$–C$_8$)cycloalkoxyamino; (C$_6$–C$_{10}$)aryl-(CH$_2$)$_t$-oxyamino, wherein t is an integer from zero to three, wherein the (C$_6$–C$_{10}$)aryl moiety of said (C$_6$–C$_{10}$)aryl-(CH$_2$)$_t$-oxyamino group may optionally be substituted with one or more substituents independently selected from halogen, (C$_1$–C$_6$)alkoxy, trihalo(C$_1$–C$_6$)alkyl, amino, cyano, (C$_1$–C$_6$)alkylamino, hydroxy, (C$_1$–C$_6$)alkyl, (C$_1$–C$_6$)alkylsulfonyl, di(C$_1$–C$_6$)alkylamino, amido carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

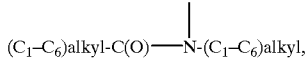

(C$_1$–C$_6$)alkyl-O—C(O)—, HC(O)—NH—, and HO—C(O)—; or a heterocycle-(CH$_2$)$_k$-amino group, wherein k is an integer from zero to three, wherein said heterocycle is selected from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinly, 1,2,5-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isoindolyl, indolyl, indazolyl, isoquinolyl, quinolyl, pthalazinyl, quinoxalinyl, quinazolinyl, cinnolinyl and benzoxazinyl; wherein the heterocycle moiety of said heterocycl-(CH$_2$)$_k$-group may be, where possible, substituted with from one to three substituents independently selected from (C$_1$–C$_6$)alkyl, halogen, hydroxy, cyano, (C$_1$–C$_6$)alkoxy, (C$_1$–C$_6$)alkylsulfonyl, trihalo(C$_1$–C$_6$)alkyl, amino, (C$_1$–C$_6$)alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, C$_1$–C$_6$)alkyl-C(O)—NH—,

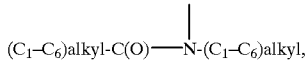

(C$_1$–C$_6$)alkyl-O—C(O)—, HC(O)—NH—, and HO—C(O)—; or R$^5$ and R$^6$ taken together may form a —(CH$_2$)$_p$W(CH$_2$)$_q$—ring wherein W is selected from

—CH$_2$—,

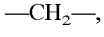

O, S, and

wherein B is selected from hydrogen and (C$_1$–C$_3$)alkyl, p is an integer from one to three and q is an integer from one to three;

R$^7$ is hydrogen or (C$_1$–C$_6$)alkyl;

R$^8$ is —CONH$_2$ or —CONHCH$_2$-NR$^{11}$R$^{12}$;

R$^9$ is hydrogen or (C$_1$–C$_6$)alkyl;

R$^{11}$ is (C$_1$–C$_6$)alkyl;

R$^{12}$ (C$_1$–C$_6$)alkyl; or $R^{11}$ and $R^{12}$ taken together form a —$(CH_2)_r$—Y—$(CH_2)_s$ ring wherein Y is

—$CH_2$—,

oxygen, sulfur or

wherein B is selected from hydrogen and $(C_1-C_3)$alkyl, r is an integer from one to three, and s is an integer from one to three;

$R^{13}$ is hydrogen, $(C_1-C_6)$alkoxy-$(CH_1-C_6)$alkyl, $(C_1-C_6)$alkyl, $(C_1-C_6)$alkoxy, $(C_3-C_6)$cycloalkyl, $(C_3-C_6)$cycloalkylmethyl, or $(C_6-C_{10})$aryl optionally substituted with one or more substitutents independently selected from fluoro, hydroxy, $(C_1-C_6)$alkoxy, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

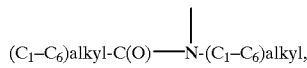

$(C_1-C_6)$alkyl-O—C(O)—, HC(O)—NH—, and HO-C(O)—; and the pharmacologically acceptable organic and inorganic salts or metal complexes.

7. A compound according to claim 6 wherein X is hydrogen, $R^1$ is methyl, and $R^8$ is —$CONH_2$.

8. A compound according to claim 7 wherein n is zero; $R^4$ is hydrogen; and $R^5$ is hydrogen.

9. A compound according to claim 8 wherein $R^6$ is halogen, amino, hydroxylamino, $(C_1-C_{12})$alkylamino optionally substituted with one or more substituents independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

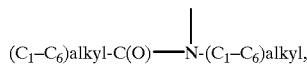

$(C_1-C_6)$alkyl-O—C(O)—, HC(O)—NH—, and HO—C(O)—; $(C_3-C_{18})$cycloalkylamino wherein the $(C_3-C_{18})$cycloalkyl moiety of said $(C_3-C_{18})$cycloalkyl amino group may optionally be substituted with one or more substituents independently selected from halogen, hydroxy, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl, $(C_1-C_6)$alkyl-C(O)—O—, 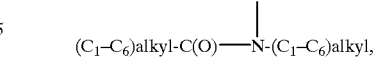

$(C_1-C_6)$alkyl-O—C(O)—, HC(O)—NH—, and HO—C(O)—; and wherein the amino moiety of said $(C_3-C_{18})$cycloalkyl amino group may optionally be substituted with $(C_1-C_6)$alkyl; di$(C_1-C_8)$alkyl-amino optionally substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

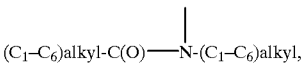

$(C_1-C_6)$alkyl-O—C(O)—, HC(O)—NH—, and HO-C(O)—; $(C_2-C_{10})$azacycloalkyl optionally substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C-C_6)$alkyl-C(O)—NH—,

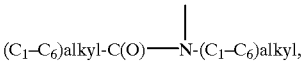

$(C_1-C_6)$alkyl-O-C(O)—, HC(O)—NH—, and HO—C(O)—; or $R^5$ and $R^6$ taken together may form a —$(CH_2)_p$W$(CH_2)_q$-ring wherein W is selected from

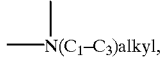

—$CH_2$—,

O, S, and

wherein B is selected from hydrogen and $(C_1-C_3)$alkyl, p is an integer from one to three, and q is an integer from one to three.

10. A compound of the formula

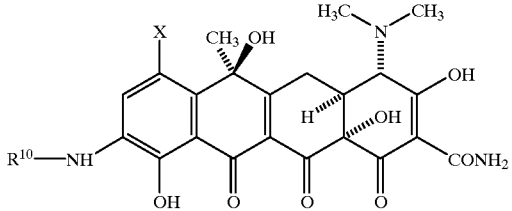

III wherein X is hydrogen;

R$^{10}$ is a group of the formula

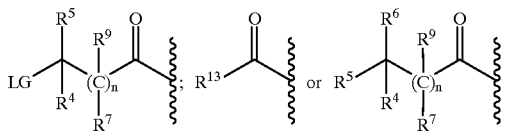

wherein n is an integer from zero to four; LG is chloro, bromo, iodo, —OSO$_2$Ph, —OSO$_2$PhCH$_3$, —OSO$_2$CH$_3$, or —OSO$_2$CF$_3$;

R$^4$ is hydrogen or (C$_1$–C$_6$)alkyl;

R$^5$ is hydrogen; (C$_1$–C$_6$)alkyl optionally substituted with one or more substituents independently selected from methylthio, (C$_1$–C$_6$)alkoxy, amino, guanidino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_{C6}$)alkyl-C(O)—NH—,

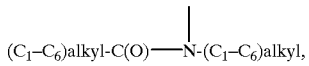

(C$_1$–C$_6$)alkyl-O—C(O)—, HC(O)—NH—, and HO—C(O)—; (C$_6$–C$_{10}$)aryl—(CH$_2$)$_h$—, wherein h is an integer from zero to three, wherein the (C$_6$–C$_{10}$)aryl moiety of said (C$_6$–C$_{10}$)aryl—(CH$_2$)$_h$ group may optionally be substituted with one or more substituents independently selected from halogen, hydroxy, (C$_1$–C$_6$)alkyl, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

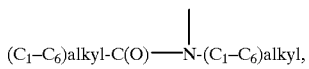

(C$_1$–C$_6$)alkyl-O—C(O)—, HC(O)—NH—, and HO-C(O)—; or (C$_3$–C$_6$)cycloalkyl—(CH$_2$)$_j$—, wherein j is an integer from zero to three, wherein the (C$_3$–C$_6$)cycloalkyl moiety of said (C$_3$–C$_6$)cycloalkyl—(CH$_2$)$_j$—group may optionally be substituted with one or more substituents independently selected from halogen, hydroxy, (C$_1$–C$_6$)alkyl, (C$_1$–C$_6$)alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

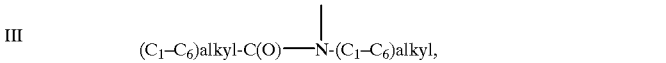

(C$_1$–C$_6$)alkyl-O—C(O)—, HC(O)—NH—, and HO—C(O)—;

R$^6$ is halogen; amino; hydroxylamino; (C$_1$–C$_{12}$) alkylamino optionally substituted with one or more substituents independently selected from halogen, hydroxy, (C$_1$–C$_6$)alkoxy, (C$_1$–C$_6$)alkylsulfonyl, trihalo (C$_1$–C$_6$)alkyl, amino, cyano, (C$_1$–C$_6$)alkylamino, di(C$_1$–C$_6$)alkylamino, amido, carboxamido, (C$_1$–C$_6$) alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

(C$_1$–C$_6$)alkyl-O—C(O)—, HC(O)—NH—, and HO—C(O)—; (C$_3$–C$_{18}$)cycloalkylamino wherein the (C$_3$–C$_{18}$) cycloalkyl moiety of said (C$_3$–C$_{18}$)cycloalkyl amino group may optionally be substituted with one or more substituents independently selected from halogen, hydroxy, (C$_1$–C$_6$) alkoxy, (C$_1$–C$_6$)alkylsulfonyl, trihalo(C$_1$–C$_6$)alkyl, amino, cyano, (C$_1$–C$_6$)alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

(C$_1$–C$_6$)alkyl-O—C(O)—, HC(O)—NH—, and HO—C(O)—; and wherein the amino moiety of said (C$_3$–C$_{18}$) cycloalkylamino group may optionally be substituted with (C$_1$–C$_6$)alkyl; di(C$_3$–C$_{18}$)cycloalkyl-amino optionally substituted with one or more substituents independently selected from halogen, hydroxy, (C$_1$–C$_6$)alkkoxy, (C$_1$–C$_6$) alkylsulfonyl, trihalo(C$_1$–C$_6$)alkyl, amino, cyano, (C$_1$–C$_6$) alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

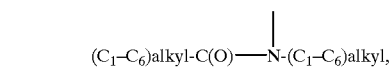

(C$_1$–C$_6$)alkyl-O—C(O)—, HC(O)—NH—, and HO—C(O)—; (C$_6$–C$_{10}$)aryl-(CH$_2$)$_m$-amino, wherein m is an integer from zero to three, wherein the (C$_6$–C$_{10}$)aryl moiety of said (C$_6$–C$_{10}$)aryl-(CH$_2$)$_m$-amino group may optionally be substituted with one or more substituents independently selected from halogen, hydroxy, (C$_1$–C$_6$)alkoxy, (C$_1$–C$_6$) alkylsulfonyl, trihalo(C$_1$–C$_6$)alkyl, amino, cyano, (C$_1$–C$_6$) alkylamino, di(C$_1$–C$_6$)alkylamino, amido, carboxamido, (C$_1$–C$_6$)alkyl, (C$_1$–C$_6$)alkyl-C(O)—O—, (C$_1$–C$_6$)alkyl-HN—C(O)—, di(C$_1$–C$_6$)alkyl-N—C(O)—, (C$_1$–C$_6$)alkyl-C(O)—NH—,

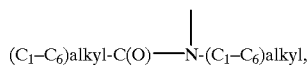

$(C_1-C_6)$alkyl-C(O)—, HC(O)—NH—, and HO—C(O)—; di($C_1-C_8$)alkyl-amino optionally substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

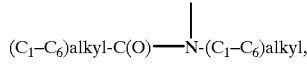

$(C_1-C_6)$alkyl-O—C(O)—, HC(O)—NH—, and HO-C(O)—; $(C_2-C_{10})$azacycloalkyl optionally substituted with one or more substituents independently selected from halogen, hydroxy, $(C_1-C_6)$alkyl, $(C_1-C_6)$alkoxy, $(C_1-C_6)$alkylsulfonyl, trihalo$(C_1-C_6)$alkyl, amino, cyano, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

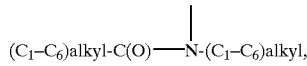

$(C_1-C_6)$alkyl-O—C(O)—, HC(O)—NH—, and HO—C(O)—; carboxy$(C_1-C_6)$alkylamino; $(C_1-C_6)$alkyl-O—C(O)-amino; $(C_1-C_6)$alkyl-O—C(O)—$(C_1-C_6)$alkylamino; $(C_1-C_6)$alkoxyamino; $(C_3-C_8)$cycloalkoxyamino; $(C_6-C_{10})$aryl—$(CH_2)_t$-oxyamino, wherein t is an integer from zero to three, wherein the $(C_6-C_{10})$aryl moiety of said $(C_6-C_{10})$aryl—$(CH_2)_t$-oxyamino group may optionally be substituted with one or more substituents independently selected from halogen, $(C_1-C_6)$alkoxy, trihalo$(C_1-C_6)$alkyl, amino, cyano, $(C_1-C_6)$alkylamino, hydroxy, $(C_1-C_6)$alkyl, $(C_1-C_6)$alkylsulfonyl, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

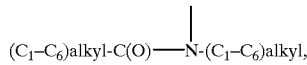

$(C_1-C_6)$alkyl-O—C(O)—, HC(O)—NH—, and HO—C(O)—; or a heterocycle—$(CH_2)_k$-amino group, wherein k is an integer from zero to three, wherein said heterocycle is selected from pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3,5-triazinyl, 1,2,5-thiadiazinyl, 1,2,5-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl; wherein the heterocycle moiety of said heterocycle-$(CH_2)_k$-group may be, where possible, substituted with from one to three substituents independently selected from $(C_1-C_6)$alkyl, halogen, hydroxy, cyano, $(C_1-C_6)$alkoxy, $(C_1-C_6)$alkylsulfonyl, trihalo$(C_1-C_6)$alkyl, amino, $(C_1-C_6)$alkylamino, di$(C_1-C_6)$alkylamino, amido, carboxamido, $(C_1-C_6)$alkyl-C(O)—O—, $(C_1-C_6)$alkyl-HN—C(O)—, di$(C_1-C_6)$alkyl-N—C(O)—, $(C_1-C_6)$alkyl-C(O)—NH—,

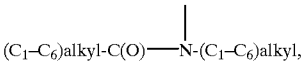

$(C_1-C_6)$alkyl-O—C(O)—, HC(O)—NH—, and HO—C(O)—; or $R^5$ and $R^6$ taken together may form a —$(CH_2)_pW(CH_2)_q$—ring wherein W is selected from

—$CH_2$—,

O, S, and

wherein B is selected from hydrogen and $(C_1-C_3)$alkyl, p is an integer from one to three, and q is an integer from one to three;

$R^7$ is hydrogen or $(C_1-C_6)$alkyl;
$R^8$ is —$CONH_2$ or —$CONHCH_2$—$Nr^{11}R^{12}$;
$R^9$ is hydrogen or $(C_1-C_6)$alkyl;
$R^{11}$ is $(C_1-C_6)$alkyl;
$R^{12}$ is $(C_1-C_6)$alkyl; or
$R^{11}$ and $R^{12}$ taken together form a —$(CH_2)_r$—Y—$(CH_2)_s$ ring wherein Y is

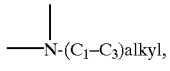

—$CH_2$—,

oxygen, sulfur or

wherein B is selected from hydrogen or $(C_1-C_3)$alkyl, r is an integer from one to three, and s is an integer from one to three;

$R^{13}$ is hydrogen, $(C_1-C_6)$alkoxy-$(C_1-C_6)$alkyl, $(C_1-C_6)$alkyl, $(C_1-C_6)$alkoxy, $(C_3-C_6)$cycloalkyl, $(C_3-C_6)$cycloalkylmethyl, or $(C_6-C_{10})$aryl optionally substituted with one or more substituents independently selected from fluoro, hydroxy, $(C_1-C_6)$alkoxy, trihalo ($C_1$–$C_6$)alkyl, amino, cyano, ($C_1$–$C_6$)alkylamino, di($C_1$–$C_6$)alkylamino, amido, carboxamido, ($C_1$–$C_6$)alkyl-C(O)—O—, ($C_1$–$C_6$)alkyl-HN—C(O)—, di($C_1$–$C_6$)alkyl-N—C(O)—, ($C_1$–$C_6$)alkyl-C(O)—NH—,

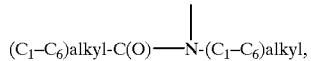

($C_1$–$C_6$)alkyl-O—C(O)—, HC(O)—NH—, and HO—C(O)—; and the pharmacologically acceptable organic and inorganic salts or metal complexes.

11. A compound according to claim 10 wherein X is hydrogen, $R^1$ is methyl, and $R^8$ is —CONH$_2$.

12. A compound according to claim 11 wherein n is zero; $R^4$ is hydrogen; and $R^5$ is hydrogen.

13. A compound according to claim 12 wherein $R^6$ is halogen, amino, hydroxylamino, ($C_1$–$C_{12}$)alkylamino optionally substituted with one or more substituents independently selected from halogen, hydroxy, ($C_1$–$C_6$)alkoxy, ($C_1$–$C_6$)alkylsulfonyl, trihalo($C_1$–$C_6$)alkyl, amino, cyano, ($C_1$–$C_6$)alkylamino, di($C_1$–$C_6$)alkylamino, amido, carboxamido, ($C_1$–$C_6$)alkyl-C(O)—O—, ($C_1$–$C_6$)alkyl-HN—C(O)—, di($C_1$–$C_6$)alkyl-N—C(O)—, ($C_1$–$C_6$)alkyl-C(O)—NH—,

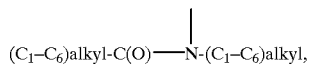

($C_1$–$C_6$)alkyl-O—C(O)—, HC(O)—NH—, and HO—C(O)—; ($C_3$–$C_{18}$)cycloalkylamino wherein the ($C_3$–$C_{18}$)cycloalkyl moiety of said ($C_3$–$C_{18}$)cycloalkyl amino group may optionally be substituted with one or more substituents independently selected from halogen, hydroxy, ($C_1$–$C_6$)alkoxy, ($C_1$–$C_6$)alkylsulfonyl, trihalo($C_1$–$C_6$)alkyl, amino, cyano, ($C_1$–$C_6$)alkylamino, di($C_1$–$C_6$)alkylamino, amido, carboxamido, ($C_1$–$C_6$)alkyl, ($C_1$–$C_6$)alkyl-C(O)—O—, ($C_1$–$C_6$)alkyl-HN—C(O)—, di($C_1$–$C_6$)alkyl-N—C(O)—, ($C_1$–$C_6$)alkyl-C(O)—NH—,

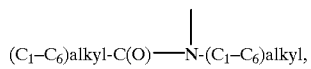

($C_1$–$C_6$)alkyl-O—C(O)—, HC(O)—NH—, and HO—C(O)—; and wherein the amino moiety of said ($C_3$–$C_{18}$)cycloalkyl amino group may optionally be substituted with ($C_1$–$C_6$)alkyl; di($C_1$–$C_8$)alkyl-amino optionally substituted with one or more substituents independently selected from halogen, hydroxy, ($C_1$–$C_6$)alkyl, ($C_1$–$C_6$)alkoxy, ($C_1$–$C_6$)alkylsulfonyl, trihalo($C_1$–$C_6$)alkyl, amino, cyano, ($C_1$–$C_6$)alkylamino, di($C_1$–$C_6$)alkylamino, amido, carboxamido, ($C_1$–$C_6$)alkyl-C(O)—O—, ($C_1$–$C_6$)alkyl-HN—C(O)—, di($C_1$–$C_6$)alkyl-N—C(O)—, ($C_1$–$C_6$)alkyl-C(O)—NH—,

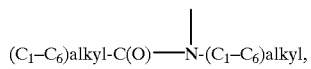

($C_1$–$C_6$)alkyl-O—C(O)—, HC(O)—NH—, and HO—C(O)—; ($C_2$–$C_{10}$)azacycloalkyl optionally substituted with one or more substituents independently selected from halogen, hydroxy, ($C_1$–$C_6$)alkyl, ($C_1$–$C_6$)alkoxy, ($C_1$–$C_6$)alkylsulfonyl, trihalo($C_1$–$C_6$)alkyl, amino, cyano, ($C_1$–$C_6$)alkylamino, di($C_1$–$C_6$)alkylamino, amido, carboxamido, ($C_1$–$C_6$)alkyl-C(O)—O—, ($C_1$–$C_6$)alkyl-HN—C(O)—, di($C_1$–$C_6$)alkyl-N—C(O)—, ($C_1$–$C_6$)alkyl-C(O)—NH—, ($C_1$–$C_6$)alkyl-C(O)—NH—,

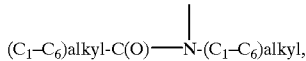

($C_1$–$C_6$)alkyl-O—C(O)—, HC(O)—NH—, and HO—C(O)—; or $R^5$ and $R^6$ taken together may form a —(CH$_2$)$_p$W(CH$_2$)$_q$—ring wherein W is selected from

—CH$_2$—,

O, S, and

wherein B is selected from hydrogen and ($C_1$–$C_3$)alkyl, p is an integer from one to three, and q is an integer from one to three.

14. A method for the prevention, treatment or control of bacterial infections in a warm-blooded animal which comprises administering to said animal a pharmacologically effective amount of a compound according to claim 1.

15. A pharmaceutical composition for the prevention, treatment or control of bacterial infections in a warm-blooded animal which comprises a pharmacologically effective amount of a compound according to claim 1 in association with a pharmaceutically acceptable carrier.

16. A method for the prevention, treatment or control of bacterial infections in a warm-blooded animal which comprises administering to said animal a pharmacologically effective amount of a compound according to claim 6.

17. A pharmaceutical composition for the prevention, treatment or control of bacterial infections in a warm-blooded animal which comprises a pharmacologically effective amount of a compound according to claim 6 in association with a pharmaceutically acceptable carrier.

18. A method for treating or preventing osteoarthritis in a mammal which comprises administering to said animal a pharmacologically effective amount of a compound according to claim 1.

19. A pharmaceutical composition for treating or preventing osteoarthritis in a mammal, which comprises a pharmacologically effective amount of a compound according to claim 1 in association with a pharmaceutically acceptable carrier.

* * * * *